United States Patent [19]

Cotrel et al.

[11] 4,220,646

[45] Sep. 2, 1980

[54] HETEROCYCLIC COMPOUNDS

[75] Inventors: Claude Cotrel, Paris; Claude Jeanmart, Brunoy; Mayer N. Messer, Bievres; Cornel Crisan, Sceaux, all of France

[73] Assignee: Rhone-Poulenc Industries, Paris, France

[21] Appl. No.: 790,801

[30] Foreign Application Priority Data

| Nov. 7, 1974 | [FR] | France | 7436963 |
|---|---|---|---|
| Sept. 4, 1975 | [FR] | France | 7527160 |
| Sept. 4, 1975 | [FR] | France | 7527161 |
| Sept. 4, 1975 | [FR] | France | 7527162 |

[22] Filed: Apr. 25, 1977

Related U.S. Application Data

[63] Continuation-in-part of Ser. No. 628,926, Nov. 5, 1975, abandoned.

[51] Int. Cl.² .............. A61K 31/385; A61K 31/495; C07D 209/048
[52] U.S. Cl. ........................... 424/250; 544/372; 544/373
[58] Field of Search ............ 260/268 BC, 268 BQ; 424/250; 544/372, 373

[56] References Cited

U.S. PATENT DOCUMENTS

| 3,119,826 | 1/1964 | Regnier et al. | 260/268 C |
| 3,847,921 | 11/1974 | Cotrel et al. | 260/268 C |
| 3,862,149 | 1/1975 | Cotrel et al. | 260/268 BC |
| 3,948,917 | 4/1976 | Jeanmart et al. | 260/268 EC |

FOREIGN PATENT DOCUMENTS

| 2301069 | 7/1973 | Fed. Rep. of Germany | 260/268 BQ |
| 46-15302 | 4/1971 | Japan | 260/268 BC |

*Primary Examiner*—Glennon H. Hollrah
*Assistant Examiner*—D. B. Springer
*Attorney, Agent, or Firm*—Stevens, Davis, Miller & Mosher

[57] ABSTRACT

Heterocyclic compounds of the formula:

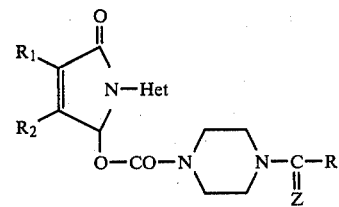

wherein the pyrroline ring and the symbols $R_1$ and $R_2$ together form an isoindoline, 6,7-dihydro-5H-pyrrolo-[3,4-b]pyrazine, 2,3,6,7-tetrahydro-5H-1,4-oxathiino-[2,3-c]pyrrole or 2,3,6,7-tetrahydro-5H-1,4-dithiino-[2,3-c]pyrrole nucleus, Het represents an optionally substituted pyrid-2-yl, quinol-2-yl or 1,8-naphthyridin-2-yl radical, Z represents oxygen or sulphur and R represents hydrogen, alkyl or halo-substituted alkyl, alkenyl, alkynyl, cycloalkyl, alkoxy, optionally substituted phenyl, phenylalkyl, the phenyl ring of which may optionally be substituted, phenylalkenyl, the phenyl ring of which may optionally be substituted, or R represents a 5- or 6-membered heterocyclic radical containing one or two hetero-atoms selected from nitrogen, oxygen and sulphur, and, when the pyrroline ring and the symbols $R_1$ and $R_2$ together form an isoindoline nucleus, the residue of the isoindoline nucleus represented by $R_1$ and $R_2$ may optionally be substituted, possess pharmacological properties, and are especially useful as tranquillizers, anti-convulsant agents, decontracturants and agents to produce hypnosis.

13 Claims, No Drawings

HETEROCYCLIC COMPOUNDS

This application is a continuation-in-part of our application Ser. No. 628,926 filed Nov. 5, 1975, now abandoned.

This invention relates to new therapeutically useful heterocyclic compounds, to processes for their preparation and pharmaceutical compositions containing them.

The new heterocyclic compounds of the present invention are those of the general formula:

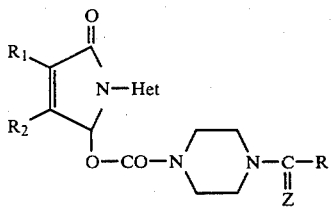

wherein the pyrroline ring and the symbols $R_1$ and $R_2$ together form an isoindoline, 6,7-dihydro-5$\underline{H}$-pyrrolo-[3,4-b]pyrazine, 2,3,6,7-tetrahydro-5$\underline{H}$-1,4-oxathiino-[2,3-c]pyrrole or 2,3,6,7-tetrahydro-5$\underline{H}$-1,4-dithiino-[2,3-c]pyrrole nucleus, Het represents a pyrid-2-yl, quinol-2-yl or 1,8-naphthyridin-2-yl radical, each such radical being optionally substituted by one, two or three atoms or radicals, which—when two or three substituents are present—may be the same or different, selected from halogen atoms (preferably chlorine), alkyl radicals containing 1 to 4 carbon atoms (preferably methyl), alkoxy radicals containing 1 to 4 carbon atoms, and the cyano radical, Z represents an oxygen or sulphur atom, and R represents a hydrogen atom, an alkyl radical containing 1 to 4 carbon atoms (e.g. methyl, ethyl, propyl or isopropyl) optionally substituted by one, two or three halogen atoms (e.g. chloromethyl or trifluoromethyl), an alkenyl radical containing 2 to 4 carbon atoms, e.g. vinyl, prop-1-enyl, isopropenyl or 2-methylprop-1-enyl, an alkynyl radical containing 2 to 4 carbon atoms, e.g. ethynyl, a cycloalkyl radical containing 3 to 6 carbon atoms, e.g. cyclopropyl or cyclohexyl, an alkoxy radical containing 1 to 4 carbon atoms, e.g. ethoxy or t.-butoxy, a phenyl radical (optionally substituted by one, two or three atoms or radicals, which—when two or three substituents are present—may be the same or different, selected from halogen atoms, alkyl radicals containing 1 to 4 carbon atoms, alkoxy radicals containing 1 to 4 carbon atoms, and the nitro and the trifluoromethyl radicals), a phenylalkyl radical of which the alkyl moiety contains 1 to 4 carbon atoms and the phenyl ring of which may optionally be substituted as indicated above, a phenylalkenyl radical of which the alkenyl moiety contains 2 to 4 carbon atoms and the phenyl ring of which may optionally be substituted as indicated above, or R represents a 5- or 6-membered heterocyclic radical containing one or two hetero atoms selected from nitrogen, oxygen and sulphur (e.g. 4-pyridyl), and, when the pyrroline ring and the symbols $R_1$ and $R_2$ together form an isoindoline nucleus, the residue of the isoindoline nucleus represented by $R_1$ and $R_2$ may optionally be substituted by one to four atoms or radicals, which—when two or more substituents are present—may be the same or different, selected from halogen atoms (preferably chlorine), alkyl radicals containing 1 to 4 carbon atoms, alkoxy radicals containing 1 to 4 carbon atoms, and the nitro and trifluoromethyl radicals.

It is to be understood that the alkyl, alkoxy, alkenyl and alkynyl radicals, or alkyl or alkenyl moieties of phenylalkyl and phenylalkenyl radicals, mentioned above in respect of the definitions of symbols in general formula I may have straight- or branched-chains.

According to a feature of the present invention, the compounds of general formula I, wherein Z represents an oxygen atom and the other symbols are as hereinbefore defined, are prepared by the process which comprises reacting an acid of the general formula:

R—COOH  II (wherein R is as hereinbefore defined) or a derivative of the acid such as a halide (preferably chloride), the anhydride, a mixed anhydride or the azide, with a compound of the general formula:

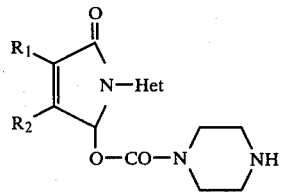

wherein the various symbols are as hereinbefore defined.

When an acid of general formula II (R being other than an alkoxy radical) is used, the reaction is generally carried out in an inert organic solvent, e.g. acetonitrile, methylene chloride, dimethylformamide or ethyl acetate, in the presence of a condensation agent such as N,N'-dicyclohexylcarbodiimide or N,N-carbonyldiimidazole, at a temperature between 20° and 60° C.

When a halide (preferably chloride) of the acid of general formula II is used, the reaction is generally carried out in an organic solvent, e.g. methylene chloride, in the presence of an acid-binding agent, for example pyridine or triethylamine, at a temperature between 0° and 30° C.

When an anhydride or a mixed anhydride of the acid of general formula II is used, the reaction is generally carried out by heating the reactants at a temperature between 30° and 100° C.

When the azide of the acid of general formula II is used, the reaction is generally carried out in an organic solvent, e.g. dioxan, in the presence of magnesium oxide at a temperature between 25° and 60° C.

The compounds of general formula III can be obtained by the action of piperazine on a mixed carbonate of the general formula:

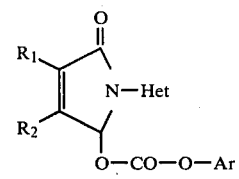

wherein the symbols $R_1$, $R_2$ and Het are as hereinbefore defined, and Ar represents a phenyl radical optionally substituted by an alkyl radical containing 1 to 4 carbon atoms or the nitro radical. The reaction is generally carried out in an anhydrous organic solvent, e.g. acetonitrile or dimethylformamide, at a temperature between 20° and 80° C.

The mixed carbonates of the general formula IV can be obtained by reaction of a chloroformate of the general formula:

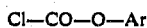   V (wherein Ar is as hereinbefore defined) with a compound of the general formula:

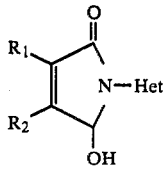   VI wherein the various symbols are as hereinbefore defined. The reaction is generally carried out in a basic organic solvent such as pyridine, and preferably at a temperature between 5° and 60° C.

The compounds of general formula VI can be obtained by partial reduction of an imide of the general formula:

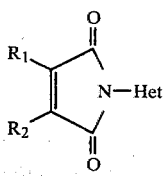   VII wherein the various symbols are as hereinbefore defined. The reduction is generally effected by means of an alkali metal borohydride in an aqueous-organic or organic solution, for example in a mixture of dioxan and water, dioxan and methanol, methanol and water, ethanol and water, or tetrahydrofuran and methanol.

The partial reduction of a compound of general formula VII in which the pyrroline ring and the symbols $R_1$ and $R_2$ together form an isoindoline nucleus which is substituted as indicated above can lead to isomeric products which can be separated by physico-chemical methods such as fractional crystallisation or chromatography.

The imides of the general formula VII can be obtained by reaction of an amine of the general formula:

   VIII (wherein Het is as hereinbefore defined) with an anhydride of the general formula:

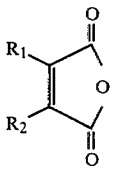   IX (wherein the symbols $R_1$ and $R_2$ represent a ring system as defined above), the reaction taking place via an intermediate product of the general formula:

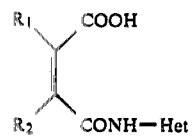   X wherein the various symbols are as hereinbefore defined. The reaction of the amine of the general formula VIII with the acid anhydride of the general formula IX is generally carried out by heating in an organic solvent, e.g. ethanol, acetic acid, dimethylformamide, acetonitrile or diphenyl ether, or in dimethylformamide in the presence of N,N'-dicyclohexylcarbodiimide and N-hydroxysuccinimide.

The cyclisation of the intermediate product of general formula X to an imide of general formula VII can generally be carried out either by heating with acetic anhydride or with acetyl chloride in acetic acid or acetic anhydride, or by the action of a condensation agent such as N,N'-dicyclohexylcarbodiimide in dimethylformamide at a temperature of about 20° C., or by the action of thionyl chloride or by heating.

With reference to general formula IX, the anhydride of pyrazine-2,3-dicarboxylic acid can be prepared in accordance with the method described by S. Gabriel and A. Sonn, Chem. Ber., 40, 4850 (1907), that of 5,6-dihydro-1,4-oxathiin-2,3-dicarboxylic acid in accordance with the method of P. ten Haken, J. Het. Chem., 7, 1211 (1970), and that of 5,6-dihydro-1,4-dithiin-2,3-dicarboxylic acid in accordance with the method of H. R. Schweizer, Helv. Chim. Acta., 52, 2229 (1969).

The compounds of general formula III can also be obtained from a compound of the general formula:

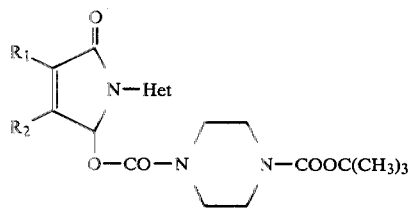   XI (wherein the various symbols are as hereinbefore defined) by treatment with trifluoroacetic acid at a temperature between 0° and −10° C.

The compounds of general formula XI can be obtained by reaction of 4-chlorocarbonyl-1-t.-butoxycarbonylpiperazine on a compound of general formula VI. The reaction is generally carried out on an alkali metal derivative of a compound of general formula VI, optionally prepared in situ, operating in an organic solvent, e.g. dimethylformamide, at a temperature which is below 20° C. and preferably between 0° and 10° C.

4-Chlorocarbonyl-1-t.-butoxycarbonylpiperazine can be obtained by the action of phosgene dissolved in toluene, at a temperature of about −5° C., on 1-t.-butoxycarbonylpiperazine.

1-t.-Butoxycarbonylpiperazine can be obtained by the action of piperazine hydrochloride on t.-butyl azidoformate.

The compounds of general formula VI in which the pyrroline ring and the symbols $R_1$ and $R_2$ together form an isoindoline nucleus which is substituted as indicated above can also be prepared in accordance with one of the following methods:

(a) when the substituent represents a halogen atom or an alkoxy radical containing 1 to 4 carbon atoms or the nitro radical, by reaction of an amine of general formula VIII with a halide of o-toluic acid substituted by a halogen atom or an alkoxy radical containing 1 to 4 carbon atoms or the nitro radical, in order to obtain a product of the general formula:

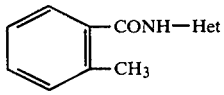   XII (wherein Het is as hereinbefore defined, and the phenyl ring is substituted as mentioned above), and cyclization of this product either by means of N-bromosuccinimide in the presence of azodiisobutyronitrile or via an intermediate gem-diester in an aqueous-organic medium, or via an intermediate dichloromethylate derivative, (b) when the substituent represents a nitro radical, by nitration of a compound of general formula VI in which the phenyl ring containing $R_1$ and $R_2$ is not substituted, or (c) when the substituent represents a halogen atom, by replacement of the nitro radical of a compound of general formula VI (wherein $R_1$ and $R_2$ together form a nitrosubstituted phenyl ring) by a halogen atom via an intermediate diazonium salt.

According to another feature of the present invention the compounds of general formula I, wherein Z represents an oxygen or sulphur atom and the other symbols are as hereinbefore defined, are prepared by the process which comprises reacting a piperazine derivative of the general formula:

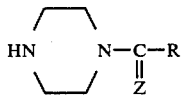   XIII (wherein Z and R are as hereinbefore defined) with a mixed carbonate of general formula IV. The reaction is generally carried out in an anhydrous organic solvent, e.g. acetonitrile or dimethylformamide, at a temperature between 20° and 100° C.

The compounds of general formula XIII, wherein Z represents an oxygen atom, can be prepared from piperazine by applying known procedures for the preparation of amides, such as the action of an acid of the general formula II or of a derivative of the acid such as a halide, an ester, the anhydride, a mixed anhydride or the azide, on piperazine. The compounds of general formula XIII can be separated from the disubstituted piperazine which is formed simultaneously by applying physical or chemical methods.

The compounds of general formula XIII, wherein Z represents a sulphur atom, can be prepared by the action of phosphorus pentasulphide on a corresponding compound of general formula XIII wherein Z represents an oxygen atom.

According to another feature of the invention, the compounds of general formula I, wherein Z represents an oxygen or sulphur atom and the other symbols are as hereinbefore defined, are prepared by the process which comprises reacting a chlorocarbonylpiperazine of the general formula:

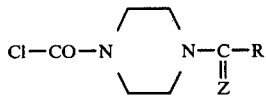   XIV (wherein R and Z are as hereinbefore defined) with a compound of general formula VI. A compound of the general formula XIV is preferably reacted with an alkali metal salt, optionally prepared in situ, of a compound of general formula VI, operating in an anhydrous organic solvent, e.g. dimethylformamide or tetrahydrofuran, at a temperature below 60° C.

According to still another feature of the invention, the compounds of general formula I, wherein Z represents a sulphur atom and the other symbols are as hereinbefore defined, are prepared by the process which comprises reacting a thioester of the general formula:

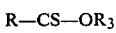   XV (wherein R is as hereinbefore defined and $R_3$ represents an alkyl radical containing 1 to 4 carbon atoms) with a compound of general formula III. The reaction is generally carried out in an organic solvent, e.g. methylene chloride, at a temperature between 0° and 40° C.

The compounds of general formula I obtained by the aforedescribed processes can optionally be purified by physical methods such as crystallisation or chromatography.

The new heterocyclic compounds of general formula I possess valuable pharmacological properties; they are particularly active as tranquillizers, anticonvulsant agents, decontracturants and agents to produce hypnosis. In animals (mice) they have proved active as such at doses of between 0.1 and 100 mg./kg. animal body weight administered orally, in particular in the following tests:

(i) electric battle according to a technique similar to that of Tedeschi et al, J. Pharmacol., 125, 28 (1959), (ii) pentetrazole-induced convulsions according to a technique similar to that of Everett and Richards, J. Pharmacol., 81, 402 (1944), (iii) supramaximal electric shock according to the technique of Swinyard et al, J. Pharmacol., 106, 319 (1952), and (iv) locomotor activity according to the technique of Courvoisier (Congrès des Médecins Aliénistes et Neurologistes-Tours—8—12th June 1959) and Julou (Bulletin de al Société de Pharmacie de Lille, No. 2, January 1967, page 7).

Furthermore, they exhibit only low toxicity; their 50% lethal dose ($LD_{50}$) in the case of mice is generally greater than 300 mg./kg. animal body weight when administered orally.

Compounds of general formula I of particular value are those wherein the pyrroline nucleus and $R_1$ and $R_2$ form an isoindoline, 6,7-dihydro-5H-pyrrolo[3,4-b]pyrazine, 2,3,6,7-tetrahydro-5H-1,4-oxathiino[2,3-c]pyrrole or 2,3,6,7-tetrahydro-5H-1,4-dithiino[2,3-c]pyrrole nucleus, Het represents a pyrid-2-yl, quinol-2-yl or 1,8-naphthyridin-2-yl radical substituted by a halogen atom (preferably chlorine), Z represents an oxygen or sulphur atom (preferably oxygen), and R represents a hydrogen atom or an alkyl radical containing 1 to 4 carbon atoms optionally substituted by three halogen atoms, an alkenyl radical containing 2 to 4 carbon atoms, an alkynyl radical containing 2 to 4 carbon atoms or an alkoxy radical containing 1 to 4 carbon atoms.

Compounds of general formula I of more especial value are those wherein the pyrroline nucleus and $R_1$ and $R_2$ form an isoindoline nucleus or a 2,3,6,7-tetrahydro-5H-1,4-dithiino[2,3-c]pyrrole nucleus, Het represents a 1,8-naphthyridin-2-yl radical substituted by a chlorine atom (preferably in the 7-position), Z represents an oxygen or sulphur atom (preferably oxygen), and R represents a hydrogen atom or an alkyl radical containing 1 to 4 carbon atoms, an alkoxy radical containing 1 to 4 carbon atoms, an alkenyl radical containing 2 to 4 carbon atoms or the trifluoromethyl radical.

Amongst the preferred class of compounds there may be mentioned particularly 3-(4-acryloylpiperazin-1-yl)carbonyloxy-2-(7-chloro-1,8-naphthyridin-2-yl)-isoindolin-1-one, 2-(7-chloro-1,8-naphthyridin-2-yl)-3-(4-methacryloylpiperazin-1-yl)carbonyloxy-isoindolin-1-one, 2-(7-chloro-1,8-naphthyridin-2-yl)-3-(4-propionyl-piperazin-1-yl)carbonyloxy-isoindolin-1-one, 2-(7-chloro-1,8-naphthyridin-2-yl)-3-(4-trifluoroacetylpiperazin-1-yl)carbonyloxy-isoindolin-1-one, 3-(4-butyrylpiperazin-1-yl)carbonyloxy-2-(7-chloro-1,8-naphthyridin-2-yl)-isoindolin-1-one, 2-(7-chloro-1,8-naphthyridin-2-yl)-3-(4-formylpiperazin-1-yl)carbonyloxy-isoindolin-1-one, 2-(7-chloro-1,8-naphthyridin-2-yl)-3-(4-thioformylpiperazin-1-yl)carbonyloxy-isoindolin-1-one, 2-(7-chloro-1,8-naphthyridin-2-yl)-3-(4-ethoxycarbonylpiperazin-1-yl)carbonyloxy-isoindolin-1-one, 2-(7-chloro-1,8-naphthyridin-2-yl)-3-[4-(3-methyl-but-2-enoyl)-piperazin-1-yl]carbonyloxy-isoindolin-1-one, and 6-(7-chloro-1,8-naphthyridin-2-yl)-7-oxo-5-(4-propionyl-piperazin-1-yl)-carbonyloxy-2,3,6,7-tetrahydro-5H-1,4-dithiino[2,3-c]pyrrole.

The following non-limitative Examples illustrate the invention.

EXAMPLE 1

Acryloyl chloride (4.9 g.) is added to a solution of 2-(7-chloro-1,8-naphthyridin-2-yl)-3-(piperazin-1-yl)carbonyloxy-isoindolin-1-one (7.6 g.) and anhydrous pyridine (18 cc.) in anhydrous methylene chloride (180 cc.), whilst keeping the temperature at about 5° C. The reaction mixture is stirred for 2 hours at a temperature of about 20° C. and then methylene chloride (100 cc.) and water (100 cc.) are added. The aqueous phase is isolated by decanting and washed with methylene chloride (2×100 cc.). The organic phases are combined, washed with water (100 cc.), dried over sodium sulphate and then evaporated to dryness under reduced pressure (20 mm.Hg). The residue obtained is dissolved in methylene chloride (40 cc.) and the solution is filtered through silica gel (125 g.) contained in a column of diameter 35 mm. Elution is carried out using methylene chloride (1,000 cc.), followed by a mixture of methylene chloride and ethyl acetate (90-10 by volume; 1,000 cc.) and a mixture of methylene chloride and ethyl acetate (75-25 by volume; 1,000 cc.). These eluates are discarded. Elution is then carried out using a mixture of methylene chloride and ethyl acetate (75-25 by volume; 4,000 cc.), and the corresponding eluate is evaporated to dryness under reduced pressure (20 mm.Hg). The residue is recrystallised from acetonitrile (90 cc.). A product which melts at about 140° C. is thus obtained and is dissolved in dimethylformamide (15 cc.) at a temperature of about 50° C. The solution obtained is poured into water (200 cc.) and the product which is insolubilized is filtered off and then washed with water (3×15 cc.). After drying under reduced pressure (1 mm.Hg) at a temperature of about 50° C., 3-(4-acryloyl-piperazin-1-yl)carbonyloxy-2-(7-chloro-1,8-naphthyridin-2-yl)-isoindolin-1-one (1.5 g.), which melts at 188° C., is obtained.

2-(7-Chloro-1,8-naphthyridin-2-yl)-3-(piperazin-1-yl)carbonyloxy-isoindolin-1-one can be prepared in the following manner:

Anhydrous piperazine (5.15 g.) is added to a suspension of 2-(7-chloro-1,8-naphthyridin-2-yl)-3-phenoxycarbonyloxy-isoindolin-1-one (5.2 g.) in acetonitrile (32 cc.). The reaction mixture is stirred for 1 hour at a temperature of about 20° C. and diisopropyl ether (150 cc.) is then added. The insoluble product is filtered off and washed with a mixture of acetonitrile and diisopropyl ether (50—50 by volume; 20 cc.) and then with diisopropyl ether (50 cc.). After the product thus obtained has been recrystallised from a mixture of acetonitrile and methanol (90-10 by volume; 160 cc.), 2-(7-chloro-1,8-naphthyridin-2-yl)-3-(piperazin-1-yl)-carbonyloxy-isoindolin-1-one (2.4 g.), which melts at 245° C. with decomposition, is obtained.

The 2-(7-chloro-1,8-naphthyridin-2-yl)-3-phenoxycarbonyloxy-isoindolin-1-one starting material can be prepared in the following manner:

Phenyl chloroformate (126 g.) is added to a suspension of 2-(7-chloro-1,8-naphthyridin-2-yl)-3-hydroxy-isoindolin-1-one (86.5 g.) in pyridine (980 cc.), whilst keeping the temperature at about 25° C. The reaction mixture is stirred for 3 hours at a temperature of about 20° C. and then poured into ice-water (9,000 cc.). The product which crystallises is filtered off, washed with water (6×500 cc.) and then with acetonitrile (3×200 cc.). After drying, 2-(7-chloro-1,8-naphthyridin-2-yl)-3-phenoxycarbonyloxy-isoindolin-1-one (96.7 g.), which melts at 235° C. with decomposition, is obtained.

2-(7-Chloro-1,8-naphthyridin-2-yl)-3-hydroxy-isoindolin-1-one can be prepared by adding potassium borohydride (1.72 g.) to a suspension of 2-(7-chloro-1,8-naphthyridin-2-yl)-phthalimide (17.7 g.) in dioxan (87 cc.) and a saturated aqueous solution of disodium phosphate (26.4 cc.), whilst cooling externally by means of an ice bath. After stirring for 14 hours, the mixture is allowed to return to a temperature of about 20° C. and is stirred for a further 2 hours, then a saturated aqueous solution of disodium phosphate (400 cc.) is added. The precipitate formed is filtered off and washed with cold water (225 cc.). After drying in air, 2-(7-chloro-1,8-naphthyridin-2-yl)-3-hydroxyisoindolin-1-one (17.5 g.), which melts at 248° C., is obtained.

2-(7-Chloro-1,8-naphthyridin-2-yl)-phthalimide can be prepared by heating a mixture of 2-(7-hydroxy-1,8-naphthyridin-2-yl)-phthalimide (26.3 g.) with phosphorus oxychloride (79 cc.) and dimethylformamide (3.5 cc.) under reflux until gas ceases to be evolved. After cooling, the reaction mixture is poured into icewater (650 cc.) without exceeding 25° C. The product obtained is filtered off, washed with water (150 cc.) and dried to constant weight. 2-(7-Chloro-1,8-naphthyridin-2-yl)-phthalimide (24.1 g.), which melts at 268° C., is thus obtained.

2-(7-Hydroxy-1,8-naphthyridin-2-yl)-phthalimide can be prepared by heating a mixture of 2-amino-7-hydroxy-1,8-naphthyridine (25 g.) with phthalic anhydride (70 g.) in acetic acid (1,400 cc.) under reflux for 3 hours. After cooling, an amount of insoluble matter is immediately filtered off. The filtrate is seeded and the crystals obtained are filtered off and washed successively with diethyl ether (60 cc.), water (90 cc.), a saturated solution of sodium bicarbonate (120 cc.) and finally water (60 cc.). The crystals are dried to constant weight and 2-(7-hydroxy-1,8-naphthyridin-2-yl)phthalimide (17 g.), which melts at 370° C., is thus obtained.

2-Amino-7-hydroxy-1,8-naphthyridine can be prepared in accordance with the method described by S. Carboni et al, Gazz. Chim. Ital., 95, 1498 (1965).

EXAMPLE 2

Acetyl chloride (1.2 g.) is added to a solution of 2-(7-chloro-1,8-naphthyridin-2-yl)-3-(piperazin-1-yl)carbonyloxy-isoindolin-1-one (2.16 g.) and anhydrous pyridine (5 cc.) in anhydrous methylene chloride (50 cc.), whilst keeping the temperature at about 20° C. The suspension thus obtained is stirred for a further half hour and water (25 cc.) is then added. The aqueous phase is isolated by decantation and washed with methylene chloride (2×15 cc.). The organic phases are combined, washed by decantation with water (25 cc.), dried over sodium sulphate and then evaporated to dryness under reduced pressure. On recrystallising the residue from acetonitrile (45 cc.), 3-(4-acetylpiperazin-1-yl)carbonyloxy-2-(7-chloro-1,8-naphthyridin-2-yl)-isoindolin-1-one (2 g.) which melts at 224° C., is obtained.

EXAMPLE 3

Following the procedure of Example 2 but starting with 2-(7-chloro-1,8-naphthyridin-2-yl)-3-(piperazin-1-yl)carbonyloxy-isoindolin-1-one (4.24 g.), benzoyl chloride (4.22 g.) and anhydrous pyridine (10 cc.) in anhydrous methylene chloride (100 cc.), 3-(4-benzoylpiperazin-1-yl)carbonyloxy-2-(7-chloro-1,8-naphthyridin-2-yl)-isoindolin-1-one (2.15 g.), which melts at 216° C., is obtained.

EXAMPLE 4

A suspension of 2-(7-chloro-1,8-naphthyridin-2-yl)-3-phenoxycarbonyloxy-isoindolin-1-one (9.35 g.) and 1-cyclopropylcarbonylpiperazine (16.6 g.) in acetonitrile (93 cc.) is heated at a temperature of about 55° C. for 3 hours. The reaction mixture is then evaporated to dryness under reduced pressure (20 mm.Hg) and the residue obtained is taken up in methylene chloride (100 cc.) and water (50 cc.). The organic phase is isolated by decantation and then washed with water (2×25 cc.). The organic phases are combined, washed with water (3×25 cc.), dried over sodium sulphate and then evaporated to dryness under reduced pressure (20 mm.Hg). The residue obtained is dissolved in methylene chloride (45 cc.) and the solution is filtered through silica gel (220 g.) contained in a column of diameter 40 mm. Elution is carried out using methylene chloride (500 cc.), a mixture of methylene chloride and ethyl acetate (95-5 by volume; 500 cc.), a mixture of methylene chloride and ethyl acetate (90-10 by volume; 500 cc.) and a mixture of methylene chloride and ethyl acetate (70-30 by volume; 500 cc.). These eluates are discarded. Elution is then carried out using a mixture of methylene chloride and ethyl acetate (50—50 by volume; 500 cc.) and then using a mixture of methylene chloride and ethyl acetate (25-75 by volume; 500 cc.); the corresponding eluates are combined and evaporated to dryness under reduced pressure (20 mm.Hg). The residue obtained is then recrystallised from acetonitrile (290 cc.). After drying, 2-(7-chloro-1,8-naphthyridin-2-yl)-3-(4-cyclopropylcarbonylpiperazin-1-yl)-carbonyloxy-isoindolin-1-one (2.6 g.), which melts at 252° C., is obtained.

1-Cyclopropylcarbonylpiperazine can be prepared by heating a mixture of anhydrous piperazine (86 g.) and ethyl cyclopropylcarboxylate (57 g.) for 48 hours in an autoclave at a temperature of about 150° C. On fractional distillation of the crude reaction mixture, 1-cyclopropylcarbonylpiperazine (38 g., b.p. 125°-130° C./1 mm.Hg) is obtained.

EXAMPLE 5

A suspension of 2-(7-chloro-1,8-naphthyridin-2-yl)-3-phenoxycarbonyloxy-isoindolin-1-one (4.32 g.) and 3-ethoxycarbonylpiperazine (7.9 g.) in acetonitrile (27 cc.) is heated at a temperature of about 50° C. for 7 hours. After cooling, diisopropyl ether (60 cc.) is added; the insoluble product is filtered off and washed with diisopropyl ether (2×10 cc.). After this product has been recrystallised from acetonitrile (100 cc.), 2-(7-chloro-1,8-naphthyridin-2-yl)-3-(4-ethoxycarbonylpiperazin-1-yl)carbonyloxy-isoindolin-1-one (3.2 g.), which melts at 211° C., is obtained.

1-Ethoxycarbonylpiperazine can be prepared according to the method described by T. S. Moore et al, J. Chem. Soc. 45 (1929).

EXAMPLE 6

Acetyl chloride (1.33 g.) is added to a suspension of 6-(7-chloro-1,8-naphthyridin-2-yl)-7-oxo-5-(piperazin-1-yl)carbonyloxy-6,7-dihydro-5H-pyrrolo[3,4-b]pyrazine (2.4 g.) in anhydrous methylene chloride (56 cc.) and anhydrous pyridine (5.6 cc.). The reaction mixture is stirred for 1 hour at a temperature of about 25° C. and water (35 cc.) is then added. The aqueous phase is isolated by decantation and extracted with methylene chloride (2×20 cc.). The organic phases are combined, washed by decantation with water (3×20 cc.), dried over sodium sulphate and then concentrated to dryness under reduced pressure. The residue obtained is dissolved in methylene chloride (48 cc.) and the resulting solution is filtered through silica gel (48 g.) contained in a column of diameter 2.4 cm. Elution is carried out using pure methylene chloride (250 cc.) followed by a mixture of methylene chloride and methanol (99-1 by volume; 200 cc.) and a mixture of methylene chloride and methanol (97.5-2.5 by volume; 150 cc.). These eluates are discarded. Elution is then carried out using a mixture of methylene chloride and methanol (97.5-2.5 by volume; 250 cc.). The corresponding eluate is concentrated to dryness under reduced pressure (20 mm.Hg). On recrystallising the residue from acetonitrile (75 cc.), 5-(4-acetylpiperazin-1-yl)carbonyloxy-6-(7-chloro-1,8-naphthyridin-2-yl)-7-oxo-6,7-dihydro-5H-pyrrolo[3,4-b]pyrazine (1.75 g.), which melts at 270° C., is obtained.

6-(7-Chloro-1,8-naphthyridin-2-yl)-7-oxo-5-(piperazin-1-yl)carbonyloxy-6,7-dihydro-5H-pyrrolo[3,4-b]pyrazine can be prepared in the following manner:

A suspension of 6-(7-chloro-1,8-naphthyridin-2-yl)-7-oxo-5-phenoxycarbonyloxy-6,7-dihydro-5H-pyrrolo[3,4-b]pyrazine (3.9 g.) and anhydrous piperazine (3.9 g.) in acetonitrile (45 cc.) is stirred at a temperature of about 20° C. for 1 hour. The insoluble product is filtered off and washed with acetonitrile (5 cc.). After drying, 6-(7-chloro-1,8-naphthyridin-2-yl)-7-oxo-5-(piperazin-1-yl)carbonyloxy-6,7-dihydro-5H-pyrrolo[3,4-b]pyrazine (2.5 g.), which decomposes at about 255° C., is obtained.

6-(7-Chloro-1,8-naphthyridin-2-yl)-7-oxo-5-phenoxycarbonyloxy-6,7-dihydro-5H-pyrrolo[3,4-b]pyrazine can be prepared by adding phenyl chloroformate (9.4 g.) to a suspension of 6-(7-chloro-1,8-naphthyridin-2-yl)-5-hydroxy-7-oxo-6,7-dihydro-5H-pyrrolo[3,4-b]pyrazine (6.3 g.) in anhydrous pyridine (63 cc.), whilst stirring and keeping the temperature at about 5° C. When the addition is complete, the reaction mixture is heated gradually to 60° C. and this temperature is maintained for 1 hour. The cooled reaction mixture is then poured into distilled water (350 cc.), whilst keeping the temperature at about 10° C. The insoluble product is filtered off and washed successively with water (120 cc.), acetonitrile (40 cc.) and diisopropyl ether (40 cc.). After drying, 6-(7-chloro-1,8-naphthyridin-2-yl)-7-oxo-5-phenoxycarbonyloxy-6,7-dihydro-5H-pyrrolo[3,4-b]pyrazine (7.2 g.), which melts at 270° C., is obtained.

6-(7-Chloro-1,8-naphthyridin-2-yl)-5-hydroxy-7-oxo-6,7-dihydro-5H-pyrrolo[3,4-b]pyrazine can be prepared by adding potassium borohydride (0.97 g.) to a suspension of 6-(7-chloro-1,8-naphthyridin-2-yl)-5,7-dioxo-6,7-dihydro-5H-pyrrolo[3,4-b]pyrazine (7.45 g.) in a mixture of dioxan and methanol (50—50 by volume; 288 cc.), whilst stirring and keeping the temperature at about 3° C. After stirring for 2 hours at a temperature of about 3° C., the insoluble product is filtered off and washed successively with a mixture of dioxan and methanol (50—50 by volume; 24 cc.), water (24 cc.), a mixture of dioxan and methanol (50—50 by volume; 24 cc.) and diisopropyl ether (12 cc.). After drying, 6-(7-chloro-1,8-naphthyridin-2-yl)-5-hydroxy-7-oxo-6,7-dihydro-5H-pyrrolo[3,4-b]pyrazine (5.3 g.), which melts at 270° C. with decomposition, is obtained.

6-(7-Chloro-1,8-naphthyridin-2-yl)-5,7-dioxo-6,7-dihydro-5H-pyrrolo[3,4-b]pyrazine can be prepared by adding 6-(7-hydroxy-1,8-naphthyridin-2-yl)-5,7-dioxo-6,7-dihydro-5H-pyrrolo[3,4-b]pyrazine (32 g.) to a solution of dimethylformamide (3.8 cc.) in phosphorus oxychloride (128 cc.), the addition being carried out gradually, at a temperature of about 15° C. When the addition is complete, the reaction mixture is heated under reflux for half an hour, then cooled and poured in small portions into crushed ice (1.3 kg.). The insoluble product is filtered off and washed with water until the wash liquors are at pH 5. After drying, 6-(7-chloro-1,8-naphthyridin-2-yl)-5,7-dioxo-6,7-dihydro-5H-pyrrolo[3,4-b]pyrazine (21.3 g.), which melts at about 340° C., with decomposition, is obtained.

6-(7-Hydroxy-1,8-naphthyridin-2-yl)-5,7-dioxo-6,7-dihydro-5H-pyrrolo[3,4-b]pyrazine can be prepared by heating a suspension of 2-amino-7-hydroxy-1,8-naphthyridine (22.4 g.) and pyrazine-2,3-dicarboxylic acid anhydride (23 g.) in acetic acid (280 cc.) under reflux. After refluxing for 1 hour, the reaction mixture is cooled to a temperature of about 30° C. and acetic anhydride (280 cc.) is then added. The reaction mixture is again heated under reflux for 10 minutes and is then cooled to a temperature of about 20° C. The insoluble product is filtered off and washed with acetic acid (40 cc.) and diisopropyl ether (200 cc.). After drying, 6-(7-hydroxy-1,8-naphthyridin-2-yl)-5,7-dioxo-6,7-dihydro-5H-pyrrolo[3,4-b]pyrazine (32.1 g.), which melts at 373° C., is obtained.

2-Amino-7-hydroxy-1,8-naphthyridine can be prepared in accordance with the method described by S. Carboni et al, Gazz. Chim. Ital., 95, 1498 (1965).

EXAMPLE 7

A solution of acrylic acid (0.93 g.) in anhydrous methylene chloride (10 cc.) followed by a solution of N,N'-dicyclohexylcarbodiimide (2.66 g.) in anhydrous methylene chloride (25 cc.) are added successively, at a temperature of about 20° C., to a suspension of 6-(7-chloro-1,8-naphthyridin-2-yl)-7-oxo-5-(piperazin-1-yl)-carbonyloxy-6,7-dihydro-5H-pyrrolo[3,4-b]pyrazine (5 g.) in anhydrous methylene chloride (100 cc.). The mixture is stirred for an hour and a half at a temperature of about 20° C. The insoluble product (dicyclohexylurea) is filtered off and washed with methylene chloride (3×5 cc.). The filtrate is concentrated to dryness under reduced pressure (20 mm.Hg) and the residue obtained is taken up in diisopropyl ether (25 cc.). The insoluble product is filtered off and washed twice with diisopropyl ether (12 cc.). After drying, a product (7 g.) is obtained which is dissolved in methylene chloride (140 cc.). The solution is filtered through silica gel (140 g.) contained in a column of diameter 3.1 cm. Elution is carried out using pure methylene chloride (140 cc.), a mixture of methylene chloride and methanol (99.5–0.5 by volume; 420 cc.) and a mixture of methylene chloride and methanol (99–1 by volume; 1,700 cc.). These eluates are discarded. Elution is then carried out using a mixture of methylene chloride and methanol (98.5–1.5 by volume; 1,400 cc.) and the corresponding eluates are combined and concentrated to dryness under reduced pressure. The residue obtained is dissolved in dimethylformamide (25 cc.) heated to a temperature of about 50° C. The solution obtained is run dropwise into water (300 cc.) kept at a temperature of about 5° C. The resulting suspension is stirred for 45 minutes at this temperature and then the insoluble product is filtered off, washed with water (5×10 cc.) and diisopropyl ether (3×10 cc.). After drying, 5-(4-acryloylpiperazin-1-yl)carbonyloxy-6-(7-chloro-1,8-naphthyridin-2-yl)-7-oxo-6,7-dihydro-5H-pyrrolo[3,4-b]pyrazine hydrate (1.8 g.), which melts at 224° C., is obtained.

EXAMPLE 8

A solution of acrylic acid (1.19 g.) in anhydrous methylene chloride (10 cc.) followed by a solution of N,N'-dicyclohexylcarbodiimide (3.4 g.) in anhydrous methylene chloride (30 cc.) are added successively, at a temperature of about 20° C., to a suspension of 6-(5-chloropyrid-2-yl)-7-oxo-5-(piperazin-1-yl)carbonyloxy-6,7-dihydro-5H-pyrrolo[3,4-b]pyrazine (5.6 g.) in anhydrous methylene chloride (100 cc.). The mixture is stirred for 1 hour at a temperature of about 20° C. The insoluble product (dicyclohexylurea) is filtered off and washed with methylene chloride (2×10 cc.). The filtrate is concentrated to dryness under reduced pressure and then the residue obtained is taken up in ethyl acetate (25 cc.) and a small amount of insoluble matter is filtered off. The filtrate is left to stand for 18 hours at a temperature of about 20° C. and the product which has crystallised is filtered off and washed with ethyl acetate (3×2 cc.). After drying, the product obtained (4.9 g.) is dissolved in methylene chloride (100 cc.). The solution is filtered through silica gel (100 g.) contained in a column of diameter 3 cm. Elution is carried out using pure methylene chloride (400 cc.), a mixture of methylene chloride and methanol (99–1 by volume; 300 cc.) and a mixture of methylene chloride and methanol (98–2 by volume; 300 cc.). These eluates are discarded. Elution is then carried out using a mixture of methylene chloride and methanol (98-2 by volume; 200 cc.) and the corresponding eluates are combined and concentrated to dryness under reduced pressure (20 mm.Hg). After recrystallisation from acetonitrile and drying, a product (2.3 g.), which is solvated with acetonitrile, is obtained. This product is dissolved in dimethylformamide (37 cc.) at a temperature of about 50° C. and the solution is poured into ice-water (370 cc.). The insoluble product is filtered off and washed with water (3×10 cc.). After drying, 5-(4-acryloylpiperazin-1-yl)carbonyloxy-6-(5-chloropyrid-2-yl)-7-oxo-6,7-dihydro-5H-pyrrolo[3,4-b]pyrazine hydrate (2.08 g.), which melts at about 202°–204° C., is obtained.

6-(5-Chloropyrid-2-yl)-7-oxo-5-(piperazin-1-yl)carbonyloxy-6,7-dihydro-5H-pyrrolo[3,4-b]pyrazine can be prepared in the following manner:

Anhydrous piperazine (86 g.) is added to a suspension of 6-(5-chloropyrid-2-yl)-7-oxo-5-phenoxycarbonyloxy-6,7-dihydro-5H-pyrrolo[3,4-b]pyrazine (76.4 g.) in acetonitrile (760 cc.). The reaction mixture is stirred for 5 hours at a temperature of about 20° C. and then the insoluble product is filtered off, washed with acetonitrile (3×25 cc.) and with diisopropyl ether (50 cc.). After drying, a product (30.8 g.) is obtained and is dissolved in methylene chloride (750 cc.). A small amount of insoluble matter is removed by treating the solution with decolourising charcoal (2 g.). After filtration, the solution is concentrated to dryness under reduced pressure. 6-(5-Chloropyrid-2-yl)-7-oxo-5-(piperazin-1-yl)carbonyloxy-6,7-dihydro-5H-pyrrolo[3,4-b]pyrazine (28.3 g.), which melts at 205° C., is thus obtained.

6-(5-Chloropyrid-2-yl)-7-oxo-5-phenoxycarbonyloxy-6,7-dihydro-5H-pyrrolo[3,4-b]pyrazine can be prepared in the following manner:

Phenyl chloroformate (141 g.) is added, with stirring and whilst keeping the temperature at about 5° C., to a suspension of 6-(5-chloropyrid-2-yl)-5-hydroxy-7-oxo-6,7-dihydro-5H-pyrrolo[3,4-b]pyrazine (158 g.) in anhydrous pyridine (1,580 cc.). When the addition is complete, the reaction mixture is heated to a temperature of about 60° C. The heating is continued for one hour. Water (4,750 cc.) is added to the reaction mixture after it has been cooled to a temperature of about 20° C. The product which crystallises is filtered off and washed with water (2×250 cc.), acetonitrile (150 cc.) and diisopropyl ether (250 cc.). After drying, 6-(5-chloropyrid-2-yl)-7-oxo-5-phenoxycarbonyloxy-6,7-dihydro-5H-pyrrolo[3,4-b]-pyrazine (169 g.), which melts at 193° C., is obtained.

6-(5-Chloropyrid-2-yl)-5-hydroxy-7-oxo-6,7-dihydro-5H-pyrrolo[3,4-b]pyrazine can be prepared by adding potassium borohydride (1.85 g.) to a suspension of 6-(5-chloropyrid-2-yl)-5,7-dioxo-6,7-dihydro-5H-pyrrolo[3,4-b]pyrazine (12 g.) in a mixture of dioxan and water (19-1 by volume; 120 cc.), the addition being carried out with vigorous stirring and whilst keeping the temperature at about 13° C. After stirring for 6 minutes, the reaction mixture is poured into water (600 cc.) and then neutralised with acetic acid (6 cc.). The product which crystallises is filtered off and washed with water (30 cc.). After drying, a product (8.5 g.), which melts at 245° C., is obtained and is suspended in chloroform (80 cc.). After stirring for half an hour at a temperature of about 20° C., the insoluble product is filtered off and washed with chloroform (30 cc.). After drying, 6-(5-chloropyrid-2-yl)-5-hydroxy-7-oxo-6,7-dihydro-5H-pyrrolo[3,4-b]-pyrazine (7.7 g.), which melts at 242° C., is obtained.

6-(5-Chloropyrid-2-yl)-5,7-dioxo-6,7-dihydro-5H-pyrrolo[3,4-b]pyrazine can be prepared by heating a suspension of 3-(5-chloropyrid-2-yl)carbamoyl-pyrazine-2-carboxylic acid (100 g.) in thionyl chloride (500 cc.) gradually to the reflux temperature. When the evolution of gas is complete, the solution obtained is evaporated to dryness under reduced pressure. The resulting residue is treated with diethyl ether (250 cc.) and the insoluble product is filtered off. After drying, a product (91 g.), which melts at 236° C., is obtained and is suspended in water (910 cc.) and chloroform (3,800 cc.). After stirring for one hour at a temperature of about 20° C., a small amount of insoluble matter is filtered off. The organic layer is decanted, dried over sodium sulphate and then concentrated to dryness under reduced pressure. 6-(5-Chloropyrid-2-yl)-5,7-dioxo-6,7-dihydro-5H-pyrrolo[3,4-b]pyrazine (72 g.), which melts at 237° C., is thus obtained.

3-(5-Chloropyrid-2-yl)carbamoyl-pyrazine-2-carboxylic acid can be prepared by heating a suspension of 2-amino-5-chloropyridine (100 g.) and pyrazine-2,3-dicarboxylic acid anhydride (58.5 g.) in acetonitrile (1,170 cc.) under reflux for one and a half hours. After cooling, the insoluble product is filtered off and washed with acetonitrile (350 cc.). After drying, a product (164 g.), which melts at 165° C., is obtained and is suspended in water (350 cc.). The suspension is acidified to pH 1 by addition of N hydrochloric acid (330 cc.) and the insoluble product is filtered off and washed with water (75 cc.). After drying, 3-(5-chloropyrid-2-yl)carbamoyl-pyrazine-2-carboxylic acid (100.9 g.), which melts at 222° C., is obtained.

Pyrazine-2,3-dicarboxylic acid anhydride can be prepared in accordance with the method described by S. Gabriel and A. Sonn, Chem. Ber., 40, 4850 (1907).

2-Amino-5-chloropyridine can be prepared in accordance with the method described by F. Friedrich et al, Pharmazie, 19 (10), 677 (1964).

EXAMPLE 9

Following the procedure of Example 8 but starting with 6-(7-chloroquinol-2-yl)-7-oxo-5-(piperazin-1-yl)carbonyloxy-6,7-dihydro-5H-pyrrolo[3,4-b]pyrazine (6.37 g.), acrylic acid (1.19 g.) and N,N'-dicyclohexylcarbodiimide (3.4 g.) in methylene chloride (170 cc.), 5-(4-acryloylpiperazin-1-yl)carbonyloxy-6-(7-chloroquinol-2-yl)-6,7-dihydro-5H-pyrrolo[3,4-b]pyrazine (0.87 g.), which melts at 226° C. after undergoing a transformation at about 150° C., is obtained.

6-(7-Chloroquinol-2-yl)-7-oxo-5-(piperazin-1-yl)carbonyloxy-6,7-dihydro-5H-pyrrolo[3,4-b]pyrazine can be prepared in a manner similar to that described in Example 1 for the preparation of 2-(7-chloro-1,8-naphthyridin-2-yl)-3-(piperazin-1-yl)carbonyloxyisoindolin-1-one but starting with 6-(7-chloroquinol-2-yl)-7-oxo-5-phenoxycarbonyloxy-6,7-dihydro-5H-pyrrolo[3,4-b]pyrazine (27 g.) and anhydrous piperazine (26.6 g.) in acetonitrile (370 cc.). 6-(7-Chloroquinol-2-yl)-7-oxo-5-(piperazin-1-yl)carbonyloxy-6,7-dihydro-5H-pyrrolo[3,4-b]pyrazine (20.2 g.), which melts at 248° C., is thus obtained.

6-(7-Chloroquinol-2-yl)-7-oxo-5-phenoxycarbonyloxy-6,7-dihydro-5H-pyrrolo[3,4-b]pyrazine, which melts at 242° C., can be prepared by the action of phenyl chloroformate on 6-(7-chloroquinol-2-yl)-5-hydroxy-7-oxo-6,7-dihydro-5H-pyrrolo[3,4-b]pyrazine in anhydrous pyridine at a temperature of about 60° C.

6-(7-Chloroquinol-2-yl)-5-hydroxy-7-oxo-6,7-dihydro-5H-pyrrolo[3,4-b]pyrazine, which melts at 256°–257° C., can be prepared by the action of potassium borohydride on 6-(7-chloroquinol-2-yl)-5,7-dioxo-6,7-dihydro-5H-pyrrolo[3,4-b]pyrazine in a dioxan-water medium (95-5 by volume) at a temperature of about 20° C.

6-(7-Chloroquinol-2-yl)-5,7-dioxo-6,7-dihydro-5H-pyrrolo[3,4-b]pyrazine, which melts at 253° C., can be prepared by the action of pyrazine-2,3-dicarboxylic acid anhydride on 2-amino-7-chloroquinoline in acetic anhydride at a temperature of about 130° C.

2-Amino-7-chloroquinoline can be prepared by heating a mixture of 2,7-dichloroquinoline (36.7 g.) and 16 N ammonia (700 cc.) in an autoclave at 125° C. for 25 hours. After cooling, the insoluble product is filtered off and then washed with water (120 cc.). After drying, a product (34 g.), which melts at about 115°–120° C., is obtained. On recrystallisation from benzene (150 cc.), 2-amino-7-chloroquinoline (10 g.), which melts at 175° C., is obtained.

2,7-Dichloroquinoline can be prepared in accordance with the method described by R. E. Lutz et al, J. Amer. Chem. Soc., 68, 1322 (1946).

EXAMPLE 10

Acetyl chloride (1.71 g.) is added to a suspension of 6-(5-methylpyrid-2-yl)-7-oxo-5-(piperazin-1-yl)carbonyloxy-6,7-dihydro-5H-pyrrolo[3,4-b]pyrazine (2.6 g.) in anhydrous methylene chloride (80 cc.) and anhydrous pyridine (7 cc.). The reaction mixture is stirred for 1 hour at a temperature of about 25° C. and water (90 cc.) is then added. The aqueous phase is separated by decantation and extracted with methylene chloride (3×30 cc.). The organic phases are combined, washed by decantation with distilled water (3×50 cc.), dried over sodium sulphate and then concentrated to dryness under reduced pressure (20 mm.Hg). The residue obtained is taken up in diisopropyl ether (50 cc.) and the insoluble product is filtered off and washed with diisopropyl ether (3×20 cc.). After drying, the product obtained (2.6 g.) is dissolved in methylene chloride (45 cc.). The resulting solution is filtered through silica gel (51 g.) contained in a column of diameter 2.4 cm. Elution is carried out using pure methylene chloride (300 cc.), a mixture of methylene chloride and methanol (99.5-0.5 by volume; 400 cc.) and a mixture of methylene chloride and methanol (99-1 by volume; 500 cc.). These eluates are discarded. Elution is then carried out using a mixture of methylene chloride and methanol (98-2 by volume; 600 cc.) and the corresponding eluates are combined and concentrated to dryness under reduced pressure (20 mm.Hg). On recrystallisation of the residue from acetonitrile (18 cc.), 5-(4-acetylpiperazin-1-yl)carbonyloxy-6-(5-methylpyrid-2-yl)-7-oxo-6,7-dihydro-5H-pyrrolo[3,4-b]-pyrazine (1.3 g.), which melts at 200° C., is obtained.

6-(5-Methylpyrid-2-yl)-7-oxo-5-(piperazin-1-yl)carbonyloxy-6,7-dihydro-5H-pyrrolo[3,4-b]pyrazine can be prepared from 6-(5-methylpyrid-2-yl)-7-oxo-5-phenoxycarbonyloxy-6,7-dihydro-5H-pyrrolo[3,4-b]pyrazine (15 g.) and anhydrous piperazine (17.8 g.) in acetonitrile (150 cc.). 6-(5-Methylpyrid-2-yl)-7-oxo-5-(piperazin-1-yl)carbonyloxy-6,7-dihydro-5H-pyrrolo-[3,4-b]pyrazine (9.85 g.), which melts at 182° C., is thus obtained.

6-(5-Methylpyrid-2-yl)-7-oxo-5-phenoxycarbonyloxy-6,7-dihydro-5H-pyrrolo[3,4-b]pyrazine can be prepared in the following manner:

Phenyl chloroformate (16.4 g.) is run, over the course of 10 minutes, at a temperature of about 20° C., into a suspension of 5-hydroxy-6-(5-methylpyrid-2-yl)-7-oxo-6,7-dihydro-5H-pyrrolo[3,4-b]pyrazine (8.47 g.) in anhydrous pyridine (110 cc.). The reaction mixture is stirred for 3 hours at a temperature of about 20° C. and is then cooled to a temperature of about 5° C. Water (350 cc.) is then added over the course of 15 minutes. The insoluble product is filtered off, washed with water (4×50 cc.), acetonitrile (2×25 cc.) and diisopropyl ether (2×30 cc.). After drying, 6-(5-methylpyrid-2-yl)-7-oxo-5-phenoxycarbonyloxy-6,7-dihydro-5H-pyrrolo[3,4-b]pyrazine (11.8 g.), which melts at 176° C., is obtained.

5-Hydroxy-6-(5-methylpyrid-2-yl)-7-oxo-6,7-dihydro-5H-pyrrolo[3,4-b]pyrazine can be prepared in the following manner:

Potassium borohydride (5.4 g.) is added to a suspension of 6-(5-methylpyrid-2-yl)-5,7-dioxo-6,7-dihydro-5H-pyrrolo[3,4-b]pyrazine (32 g.) in a mixture of dioxan and water (95-5 by volume; 320 cc.), whilst keeping the temperature at about 5° C. The reaction mixture is stirred for 30 minutes at a temperature of about 15° C. and is then poured into a 4% aqueous solution of ice-cold disodium phosphate (3,000 cc.). After standing for one hour at a temperature of about 20° C., the insoluble product is filtered off and washed with water (3×150 cc.) and then with acetonitrile (50 cc.). On recrystallisation of the product from a mixture of acetonitrile and chloroform (85-15 by volume; 1,000 cc.), 5-hydroxy-6-(5-methylpyrid-2-yl)-7-oxo-6,7-dihydro-5H-pyrrolo[3,4-b]pyrazine (17.6 g.), which melts at 240° C., is obtained.

6-(5-Methylpyrid-2-yl)-5,7-dioxo-6,7-dihydro-5H-pyrrolo[3,4-b]pyrazine can be prepared in the following manner:

2-Amino-5-methylpyridine (21.6 g.) is added to a suspension of pyrazine-2,3-dicarboxylic anhydride (30 g.) in acetic anhydride (300 cc.) at a temperature of about 25° C. The reaction mixture is stirred for 10 minutes at this temperature and then heated at a temperature of about 100° C. for 15 minutes. After cooling to a temperature of about 50° C., diisopropyl ether (600 cc.) is added and cooling is continued to 5° C. After stirring for one hour at this temperature, the insoluble product is filtered off and washed with diisopropyl ether (3×50 cc.). After drying, 6-(5-methylpyrid-2-yl)-5,7-dioxo-6,7-dihydro-5H-pyrrolo-[3,4-b]pyrazine (32 g.), which melts at 240° C., is obtained.

EXAMPLE 11

Following the procedure of Example 10 but starting with 6-(5-methylpyrid-2-yl)-7-oxo-5-(piperazin-1-yl)carbonyloxy-6,7-dihydro-5H-pyrrolo[3,4-b]pyrazine (2.2 g.) and benzoyl chloride (2.62 g.) in anhydrous methylene chloride (60 cc.) and in the presence of anhydrous pyridine (6 cc.), 5-(4-benzoylpiperazin-1-yl)-carbonyloxy-6-(5-methylpyrid-2-yl)-7-oxo-6,7-dihydro-5H-pyrrolo[3,4-b]pyrazine (2.07 g.), which melts at 194° C., is obtained.

EXAMPLE 12

Following the procedure of Example 8 but starting with 6-(5-methylpyrid-2-yl)-7-oxo-5-(piperazin-1-yl)carbonyloxy-6,7-dihydro-5H-pyrrolo[3,4-b]pyrazine (14.35 g.), acrylic acid (3.2 g.) and N,N'-dicyclohexylcarbodiimide (9.25 g.) in anhydrous methylene chloride (350 cc.), 5-(4-acryloylpiperazin-1-yl)-carbonyloxy-6-(5-methylpyrid-2-yl)-7-oxo-6,7-dihydro-5H-pyrrolo[3,4-b]pyrazine (2.45 g.), which melts at 221° C., is obtained.

EXAMPLE 13

Following the procedure of Example 10 but starting with 6-(7-chloroquinol-2-yl)-7-oxo-5-(piperazin-1-yl)carbonyloxy-6,7-dihydro-5H-pyrrolo[3,4-b]pyrazine (6 g.) and acetyl chloride (3.3 g.) in anhydrous methylene chloride (160 cc.) and in the presence of anhydrous pyridine (16 cc.), 5-(4-acetylpiperazin-1-yl)carbonyloxy-6-(7-chloroquinol-2-yl)-7-oxo-6,7-dihydro-5H-pyrrolo[3,4-b]pyrazine (4.5 g.), which melts at 270° C., is obtained.

EXAMPLE 14

Formic acid (0.46 g.) is added to a solution of 2-(7-chloro-1,8-naphthyridin-2-yl)-3-(piperazin-1-yl)carbonyloxy-isoindolin-1-one (2.12 g.) and N,N'-dicyclohexylcarbodiimide (2.06 g.) in anhydrous methylene chloride (50 cc.). The mixture is stirred for 18 hours at a temperature of about 20° C. The precipitate is filtered off and washed with methylene chloride (10 cc.). The filtrate is concentrated to dryness. The residue resulting from the concentration process is washed with water (25 cc.). The precipitate is filtered off and dried. After recrystallisation from acetonitrile (250 cc.), 2-(7-chloro-1,8-naphthyridin-2-yl)-3-(4-formylpiperazin-1-yl)carbonyloxy-isoindolin-1-one (1.3 g.), which melts at 260° C., is obtained.

EXAMPLE 15

Propionyl chloride (1.33 cc.) is added, over the course of 3 minutes, to a suspension of 2-(7-chloro-1,8-naphthyridin-2-yl)-3-(piperazin-1-yl)carbonyloxy-isoindolin-1-one (2.12 g.) and anhydrous pyridine (5 cc.) in anhydrous methylene chloride (50 cc.). The mixture is stirred for a further 30 minutes at a temperature of about 20° C. and then water (25 cc.) is added. After decantation, the aqueous layer is washed with methylene chloride (30 cc.). The organic phases are combined and washed with water (25 cc.), then they are dried over anhydrous magnesium sulphate (10 g.). After filtration, the solution is concentrated to dryness. The residue is washed on the filter with diisopropyl ether (10 cc.), dried and then recrystallised from acetonitrile (35 cc.). After a second recrystallisation from the same solvent, 2-(7-chloro-1,8-naphthyridin-2-yl)-3-(4-propionylpiperazin-1-yl)carbonyloxy-isoindolin-1-one (1.3 g.), which melts at 221° C., is obtained.

EXAMPLE 16

Following the procedure of Example 15 but starting with 2-(7-chloro-1,8-naphthyridin-2-yl)-3-(piperazin-1-yl)carbonyloxy-isoindolin-1-one (2.12 g.), anhydrous pyridine (5 cc.) in anhydrous methylene chloride (50 cc.) and butyryl chloride (1.6 g.), 3-(4-butyrylpiperazin-1-yl)carbonyloxy-2-(7-chloro-1,8-naphthyridin-2-yl)-isoindolin-1-one (1 g.) is obtained after recrystallisation from acetonitrile (15 cc.); the product melts at 202° C.

EXAMPLE 17

Following the procedure of Example 15 but starting with 2-(7-chloro-1,8-naphthyridin-2-yl)-3-piperazin-1-yl)carbonyloxy-isoindolin-1-one (2.12 g.), anhydrous pyridine (5 cc.) in anhydrous methylene chloride (50 cc.) and isobutyryl chloride (1.6 g.), 3-(4-isobutyrylpiperazin-1-yl)carbonyloxy-2-(7-chloro-1,8-naphthyridin-2-yl)-isoindolin-1-one (2 g.) is obtained after recrystallisation from acetonitrile (150 cc.); the product melts at 254° C.

EXAMPLE 18

The procedure of Example 14 is followed but starting with 2-(7-chloro-1,8-naphthyridin-2-yl)-3-(piperazin-1-yl)carbonyloxy-isoindolin-1-one (4.23 g.), N,N'-dicyclohexylcarbodiimide (3.1 g.) in anhydrous methylene chloride (100 cc.) and cyclohexylcarboxylic acid (1.92 g.). After having filtered off the precipitate, the organic solution is washed with an 8% aqueous solution of sodium bicarbonate (20 cc.) and then dried over anhydrous potassium carbonate (10 g.). After the solution has been filtered and the filtrate concentrated to dryness, the residue is recrystallised from ethanol (300 cc.). 2-(7-Chloro-1,8-naphthyridin-2-yl)-3-(4-cyclohexylcarbonylpiperazin-1-yl)carbonyloxy-isoindolin-1-one (3.7 g.), which melts at 240° C., is thus obtained.

EXAMPLE 19

The procedure of Example 15 is followed but starting with 2-(7-chloro-1,8-naphthyridin-2-yl)-3-(piperazin-1-yl)carbonyloxy-isoindolin-1-one (2.12 g.), anhydrous pyridine (5 cc.) in anhydrous methylene chloride (50 cc.) and chloroacetyl chloride (1.7 g.). The crude product is recrystallised from acetonitrile (150 cc.). The recrystallised product is dissolved in dimethylformamide (100 cc.) at 40° C. After filtration, the solution is diluted with water (300 cc.). The resulting precipitate is filtered off, washed with water (10 cc.) and then dried. 3-(4-Chloroacetylpiperazin-1-yl)-carbonyloxy-2-(7-chloro-1,8-naphthyridin-2-yl)-isoindolin-1-one (1.4 g.), which melts at 222°-224° C., is thus obtained.

EXAMPLE 20

The procedure of Example 14 is followed but starting with 2-(7-chloro-1,8-naphthyridin-2-yl)-3-(piperazin-1-yl)carbonyloxy-isoindolin-1-one (2.12 g.), N,N'-dicyclohexylcarbodiimide (2.05 g.) in anhydrous methylene chloride (50 cc.) and trifluoroacetic acid (1.71 g.). The crude product, after it has been filtered off, is washed with diethyl ether (50 cc.). The product is then dissolved in methylene chloride (110 cc.). The solution is filtered and concentrated to dryness and the residue is washed again with diethyl ether (45 cc.). 2-(7-Chloro-1,8-naphthyridin-2-yl)-3-(4-trifluoroacetylpiperazin-1-yl)carbonyloxy-isoindolin-1-one (0.91 g.), which melts at 218° C., is thus obtained.

EXAMPLE 21

Following the prcedure of Example 1 but starting with 2-(7-chloro-1,8-naphthyridin-2-yl)-3-(piperazin-1-yl)carbonyloxy-isoindolin-1-one (4.24 g.), isonicotinoyl chloride hydrochloride (5.34 g.), triethylamine (4.04 g.) and anhydrous pyridine (10 cc.) in anhydrous methylene chloride (100 cc.), 2-(7-chloro-1,8-naphthyridin-2-yl)-3-(4-isonicotinoylpiperazin-1-yl)carbonyloxy-isoindolin-1-one (2.7 g.), which melts at 185° C., is obtained.

EXAMPLE 22

Following the procedure of Example 1 but starting with 2-(7-chloro-1,8-naphthyridin-2-yl)-3-(piperazin-1-yl)carbonyloxy-isoindolin-1-one (4.24 g.), crotonoyl chloride (3.12 g.) and anhydrous pyridine (10 cc.) in anhydrous methylene chloride (100 cc.), 2-(7-chloro-1,8-naphthyridin-2-yl)-3-(4-crotonoyl-piperazin-1-yl)carbonyloxy-isoindolin-1-one (1.7 g.), which melts at 220°–222° C., is obtained.

EXAMPLE 23

Methacrylic acid (1.3 g.) is added to a solution of 2-(7-chloro-1,8-naphthyridin-2-yl)-3-(piperazin-1-yl)carbonyloxy-isoindolin-1-one (4.24 g.) and N,N'-dicyclohexylcarbodiimide (3.1 g.) in anhydrous methylene chloride (100 cc.). The reaction mixture is stirred for 2 hours at a temperature of about 20° C., and the insoluble dicyclohexylurea is then filtered off and washed with methylene chloride (20 cc.). The filtrate is evaporated to dryness under reduced pressure and the residue obtained is dissolved in boiling ethanol (200 cc.). On cooling, a product crystallises and is filtered off and then washed successively with ethanol (10 cc.) and diisopropyl ether (25 cc.). On recrystallisation of the product from ethanol (250 cc.), 2-(7-chloro-1,8-naphthyridin-2-yl)-3-(4-methacryloylpiperazin-1-yl)carbonyloxy-isoindolin-1-one (3.3 g.), which melts at 165° C. and then at 200° C., is obtained.

EXAMPLE 24

A solution of t.-butoxycarbonylazide (3.12 cc.) in dioxan (30 cc.) is added to a suspension of 2-(7-chloro-1,8-naphthyridin-2-yl)-3-(piperazin-1-yl)carbonyloxy-isoindolin-1-one (4.24 g.) and magnesium oxide (0.81 g.) in distilled water (13 cc.). The reaction mixture is then heated at a temperature of about 40° C. for 23 hours. After cooling, water (100 cc.) and methylene chloride (100 cc.) are added to the reaction mixture. The aqueous phase is separated by decantation and then washed with water (3×25 cc.). The organic phases are combined, washed twice by decantation with water (25 cc.), dried over sodium sulphate in the presence of decolourising charcoal, filtered and evaporated to dryness under reduced pressure. The oily residue obtained is taken up in diisopropyl ether (25 cc.). The product which is insolubilized is filtered off and washed with diisopropyl ether (20 cc.). After drying, the product obtained (5.3 g.) is dissolved in methylene chloride (25 cc.). The solution is filtered through silica gel (105 g.) contained in a column of diameter 2.8 cm. Elution is carried out using methylene chloride (450 cc.) and then a mixture of methylene chloride and ethyl acetate (90-10 by volume; 200 cc.). These eluates are discarded. Elution is then carried out using a mixture of methylene chloride and ethyl acetate (90-10 by volume; 700 cc.) and the eluate is evaporated to dryness under reduced pressure. On recrystallisation of the residue from a mixture of acetonitrile and diisopropyl ether (17-83 by volume; 120 cc.), 2-(7-chloro-1,8-naphthyridin-2-yl)-3-(4-t.-butoxycarbonylpiperazin-1-yl)carbonyloxy-isoindolin-1-one (2.4 g.), which melts at 195° C., is obtained.

EXAMPLE 25

Following the procedure of Example 23 but starting with 2-(7-chloro-1,8-naphthyridin-2-yl)-3-(piperazin-1-yl)carbonyloxy-isoindolin-1-one (4.24 g.), N,N'-dicyclohexylcarbodiimide (3.1 g.) and propiolic acid (1.05 g.) in anhydrous methylene chloride (100 cc.), 2-(7-chloro-1,8-naphthyridin-2-yl)-3-(4-propioloylpiperazin-1-yl)carbonyloxy-isoindolin-1-one (3.7 g.), which melts at 265° C., is obtained.

EXAMPLE 26

Following the procedure of Example 23 but starting with 2-(7-chloro-1,8-naphthyridin-2-yl)-3-(piperazin-1-yl)carbonyloxy-isoindolin-1-one (4.24 g.), N,N'-dicyclohexylcarbodiimide (3.1 g.) and 3,3-dimethylacrylic acid (1.5 g.) in anhydrous methylene chloride (100 cc.), 2-(7-chloro-1,8-naphthyridin-2-yl)-3-[4-(3-methylbut-2-enoyl)piperazin-1-yl]carbonyloxy-isoindolin-1-one (3.5 g.), which melts at 205° C., is obtained.

EXAMPLE 27

The procedure of Example 14 is followed but starting with 6-chloro-2-(7-chloro-1,8-naphthyridin-2-yl)-3-(piperazin-1-yl)carbonyloxy-isoindolin-1-one (2.25 g.), N,N'-dicyclohexylcarbodiimide (1.5 g.) in anhydrous methylene chloride (48 cc.) and acrylic acid (0.52 g.). After having filtered off the insoluble matter formed during the reaction, the organic layer is washed with a 4% aqueous solution of sodium bicarbonate (30 cc.) and then with water (30 cc.). The organic layer is dried over anhydrous potassium carbonate (5 g.). After filtration and concentration to dryness, a crude product (3 g.) is obtained and is chromatographed on silica gel (75 g.). Elution is carried out using methylene chloride (211×100 cc.), then using methylene chloride containing 5% of ethyl acetate (47×100 cc.) and then using methylene chloride containing 10% of ethyl acetate (61×100 cc.). Fractions 120 to 320 are combined and concentrated to dryness. A product (1.4 g.) is thus obtained and is recrystallised from boiling acetonitrile (400 cc.). 3-(4-Acryloylpiperazin-1-yl)-carbonyloxy-6-chloro-2-(7-chloro-1,8-naphthyridin-2-yl)-isoindolin-1-one (0.41 g.), which melts at 272° C., is thus obtained.

EXAMPLE 28

The procedure of Example 14 is followed but starting with 6-chloro-2-(7-chloro-1,8-naphthyridin-2-yl)-3-(piperazin-1-yl)carbonyloxy-isoindolin-1-one (2.25 g.), N,N'-dicyclohexylcarbodiimide (1.5 g.) in anhydrous methylene chloride (48 cc.) and methacrylic acid (0.62 g.). After the precipitate has been filtered off, the methylene chloride solution is washed with a 4% aqueous solution of sodium bicarbonate and then with water, and is finally dried over anhydrous potassium carbonate. After filtration and concentration to dryness, a crude product (3.2 g.) is obtained and is purified by chromatography on silica gel (75 g.). Elution is carried out using methylene chloride (25×100 cc.) and then using methylene chloride containing 10% of ethyl acetate (12×100 cc.). Fractions 32 to 37 are combined and concentrated. The product obtained is recrystallised from boiling acetonitrile. 6-Chloro-2-(7-chloro-1,8-naphthyridin-2-yl)-3-(4-methacryloylpiperazin-1-yl)-carbonyloxy-isoindolin-1-one (1 g.), which melts at 211° C., is thus obtained.

EXAMPLE 29

A solution of ethyl thioformate (1.08 g.) in methylene chloride (10 cc.) is added dropwise to a filtered solution obtained from 2-(7-chloro-1,8-naphthyridin-2-yl)-3-(piperazin-1-yl)carbonyloxy-isoindolin-1-one (4.3 g.) in methylene chloride (86 cc.) cooled to 2°–3° C. The mixture is allowed to return to a temperature of about 20° C. and is then left to stand for 16 hours. The precipitate is filtered off, then dried and finally recrystallised from dimethylformamide (35 cc.). 2-(7-Chloro-1,8-naphthyridin-2-yl)-3-(4-thioformylpiperazin-1-yl)car-

21 bonyloxy-isoindolin-1-one (1.8 g.), which melts at 295° C. with decomposition, is thus obtained.

EXAMPLE 30

Triethylamine (3.03 g.) is added to a suspension of 2-(5-chloropyrid-2-yl)-3-phenoxycarbonyloxy-isoindolin-1-one (3.8 g.) and 1-ethoxycarbonylpiperazine hydrochloride (4.86 g.) in acetonitrile (50 cc.), and the mixture is stirred for 18 hours at a temperature of about 20° C. Water (100 cc.) is then added and the insoluble product is filtered off and washed with water (10 cc.). After drying, a product (4 g.) is obtained which, after recrystallisation from acetonitrile (30 cc.), gives 2-(5-chloropyrid-2-yl)-3-(4-ethoxycarbonylpiperazin-1-yl)carbonyloxy-isoindolin-1-one (2.8 g.) melting at 160° C.

EXAMPLE 31

Propionyl chloride (2.35 g.) is added to a suspension of 6-(7-chloro-1,8-naphthyridin-2-yl)-7-oxo-5-(piperazin-1-yl)carbonyloxy-2,3,6,7-tetrahydro-5H-1,4-oxathiino[2,3-c]pyrrole (3.8 g.) in methylene chloride (85 cc.) and pyridine (8.5 cc.). The reaction mixture heats up to a temperature of about 40° C. After 20 minutes, water (50 cc.) is added to the solution obtained. After 30 minutes, the organic phase is decanted and the aqueous phase is washed with methylene chloride (25 cc.). The organic fractions are combined, washed with water (2×50 cc.) and dried over magnesium sulphate. After evaporation of the solvent, the solid residue is recrystalised from a mixture of dichloroethane (50 cc.) and ethanol (100 cc.). After drying, 6-(7-chloro-1,8-naphthyridin-2-yl)-7-oxo-5-(4-propionylpiperazin-1-yl)-carbonyloxy-2,3,6,7-tetrahydro-5H-1,4-oxathiino[2,3-c]-pyrrole (1.9 g.), which melts at 240° C., is obtained.

6-(7-Chloro-1,8-naphthyridin-2-yl)-7-oxo-5-(piperazin-1-yl)carbonyloxy-2,3,6,7-tetrahydro-5H-1,4-oxathiino[2,3-c]pyrrole can be obtained by reaction of 6-(7-chloro-1,8-naphthyridin-2-yl)-7-oxo-5-phenoxycarbonyloxy-2,3,6,7-tetrahydro-5H-1,4-oxathiino[2,3-c]-pyrrole (16.2 g.) with anhydrous piperazine (15.3 g.) in acetonitrile (90 cc.) at a temperature of about 25° C. for 8 hours. After purification by chromatography, 6-(7-chloro-1,8-naphthyridin-2-yl)-7-oxo-5-(piperazin-1-yl)carbonyloxy-2,3,6,7-tetrahydro-5H-1,4-oxathiino[2,3-c]pyrrole (14 g.), which melts at 285° C. with decomposition, is obtained.

EXAMPLE 32

A solution of propiolic acid (0.52 g.) in anhydrous methylene chloride (10 cc.) is added to a suspension of 6-(7-chloro-1,8-naphthyridin-2-yl)-7-oxo-5-(piperazin-1-yl)carbonyloxy-2,3,6,7-tetrahydro-5H-1,4-oxathiino[2,3-c]pyrrole (3 g.) and N,N'-dicyclohexylcarbodiimide (1.52 g.) in anhydrous methylene chloride (70 cc.). The mixture is stirred for one and a half hours at a temperature of about 25° C. and then the insoluble product (dicyclohexylurea) is filtered off and washed with methylene chloride (3×5 cc.). The filtrate is concentrated to dryness under reduced pressure and the residue is treated with boiling ethanol (100 cc.). After cooling, the insoluble product is filtered off and washed with ethanol (20 cc.). This product is then dissolved in methylene chloride (200 cc.) and the solution is washed by decantation successively with 0.1 N methanesulphonic acid (50 cc.) and with water (2×50 cc.). After drying, the organic solution is filtered through silica gel (45 g.) contained in a column of diameter 2.2 cm. Elution is carried out using pure methylene chloride (1,000 cc.). The eluate is discarded. Elution is then carried out using a mixture of methylene chloride and methanol (99.5-0.5 by volume; 350 cc.) and the corresponding eluate is concentrated to dryness under reduced pressure (20 mm. Hg). The residue obtained is dissolved in a mixture of methylene chloride and methanol (90-10 by volume; 300 cc.) and the solution obtained is filtered and then concentrated to dryness under reduced pressure. 6-(7-Chloro-1,8-naphthyridin-2-yl)-7-oxo-5-(4-propioloylpiperazin-1-yl)carbonyloxy-2,3,6,7-tetrahydro-5H-1,4-oxathiino[2,3-c]pyrrole (0.8 g.), which melts at 302° C. with decomposition, is thus obtained.

EXAMPLE 33

Following the procedure of Example 32 but starting with 6-(7-chloro-1,8-naphthyridin-2-yl)-7-oxo-5-(piperazin-1-yl)carbonyloxy-2,3,6,7-tetrahydro-5H-1,4-oxathiino[2,3-c]-pyrrole (3 g.), acrylic acid (0.53 g.) and N,N'-dicyclohexylcarbodiimide (1.52 g.) in anhydrous methylene chloride (80 cc.), 5-(4-acryloylpiperazin-1-yl)carbonyloxy-6-(7-chloro-1,8-naphthyridin-2-yl)-7-oxo-2,3,6,7-tetrahydro-5H-1,4-oxathiino[2,3-c]pyrrole (1.1 g.), which melts at 287° C. with decomposition, is obtained.

EXAMPLE 34

Following the procedure of Example 32 but starting with 6-(7-chloro-1,8-naphthyridin-2-yl)-7-oxo-5-(piperazine-1-yl)carbonyloxy-2,3,6,7-tetrahydro-5-H-1,4-oxathiino[2,3-c]pyrrole (3 g.), formic acid (0.34 g.) and N,N'-dicyclohexylcarbodiimide (1.52 g.) in anhydrous methylene chloride (80 cc.), 6-(7-chloro-1,8-naphthyridin-2-yl)-5-(4-formylpiperazin-1-yl)-carbonyloxy-7-oxo-2,3,6,7-tetrahydro-5H-1,4-oxathiino-[2,3-c]pyrrole (2.3 g.), which melts at 305° C., is obtained.

EXAMPLE 35

Triethylamine (4.27 g.) is added to a suspension of 6-(7-chloro-1,8-naphthyridin-2-yl)-7-oxo-5-phenoxycarbonyloxy-2,3,6,7-tetrahydro-5H-1,4-oxathiino[2,3-c]-pyrrole (3.5 g.) and 1-ethoxycarbonylpiperazine hydrochloride (7.47 g.) in acetonitrile (20 cc.) and the mixture is stirred for 24 hours at a temperature of about 25° C. The reaction mixture is then poured into water (100 cc.) and the insoluble product is filtered off, washed with water (2×25 cc.) and then with diisopropyl ether (3×25 cc.). After drying, the product obtained (3.6 g.) is dissolved in methylene chloride (125 cc.) and the solution is filtered through silica gel (75 g.) contained in a column of diameter 2.7 cm. Elution is carried out using pure methylene chloride (1,500 cc.) and then using a mixture of methylene chloride and methanol (99.5-0.5 by volume; 1,000 cc.). These eluates are discarded. Elution is then carried out using a mixture of methylene chloride and methanol (99.5-0.5 by volume; 500 cc.) followed by a mixture of methylene chloride and methanol (99-1 by volume; 1,000 cc.). These eluates are combined and concentrated to dryness under reduced pressure (20 mm.Hg). 6-(7-Chloro-1,8-naphthyridin-2-yl)-5-(4-ethoxycarbonylpiperazin-1-yl)-carbonyloxy-7-oxo-2,3,6,7-tetrahydro-5H-1,4-oxathiino-[2,3-c]pyrrole (1.7 g.), which melts at 275° C., is thus obtained.

EXAMPLE 36

Butyric acid (0.71 g.) is added to a suspension of 6-(7-chloro-1,8-naphthyridin-2-yl)-7-oxo-5-(piperazin- 1-yl)carbonyloxy-2,3,6,7-tetrahydro-5H-1,4-dithiino[2,3-c]pyrrole (2.50 g.) and N,N'-dicyclohexylcarbodiimide (1.67 g.) in anhydrous methylene chloride (50 cc.) and the mixture is stirred for 1 hour at 20° C. After filtering off the dicyclohexylurea formed, washing with methylene chloride (15 cc.) and evaporating the solvent, the residue obtained (3.8 g.) is washed with boiling ethanol (35 cc.) and then recrystallised from a mixture of acetonitrile (110 cc.) and ethanol (11 cc.). 5-(4-Butyrylpiperazin-1-yl)carbonyloxy-6-(7-chloro-1,8-naphthyridin-2-yl)-7-oxo-2,3,6,7-tetrahydro-5H-1,4-dithiino[2,3-c]pyrrole (1.95 g.), which melts at 248° C., is thus obtained.

6-(7-Chloro-1,8-naphthyridin-2-yl)-7-oxo-5-(piperazin-1-yl)carbonyloxy-2,3,6,7-tetrahydro-5H-1,4-dithiino[2,3-c]pyrrole employed as starting material can be prepared in the following manner: 5-(4-t.-Butoxycarbonylpiperazin-1-yl)carbonyl-oxy-6-(7-chloro-1,8-naphthyridin-2-yl)-7-oxo-2,3,6,7-tetrahydro-5-H-1,4-dithiino[2,3-c]pyrrole (3.40 g.) is added, over the course of 20 minutes, to trifluoroacetic acid (14 cc.) cooled to between −5° and −10° C. The solution obtained at the end of the addition is kept for a further half an hour at the same temperature and is then diluted with ice-water (140 cc.). The resulting precipitate is filtered off, washed twice with distilled water (total 50 cc.) and treated, until complete dissolution has taken place, with 2N aqueous sodium hydroxide solution (100 cc.) and methylene chloride (150 cc). The organic solution is washed three times with distilled water (total 150 cc.), dried over anhydrous sodium sulphate, treated with decolourising charcoal (0.2 g.) and evaporated. The crystals obtained are washed with boiling acetonitrile (40 cc.). 6-(7-Chloro, 1,8-naphthyridin-2-yl)-7-oxo-5-(piperazin-1-yl)-carbonyloxy-2,3,6,7-tetrahydro-5-H-1,4-dithiino[2,3-c]-pyrrole (2.20 g.), which melts at 300° C. with decomposition, is obtained.

5-(4-t.-Butoxycarbonylpiperazin-1-yl)-carbonyloxy-6-(7-chloro-1,8-naphthyridin-2-yl)-7-oxo-2,3,6,7-tetrahydro-5H-1,4-dithiino[2,3-c]pyrrole can be prepared by treating 6-(7-chloro-1,8-naphthyridin-2-yl)-5-hydroxy-7-oxo-2,3,6,7-tetrahydro-5H-1,4-dithiino-[2,3-c]pyrrole (40.5 g.) with sodium hydride (3.15 g.) in anhydrous dimethylformamide (400 cc.) at 2° C., and by adding a solution of 4-chlorocarbonyl-1-t.-butoxycarbonylpiperazine (45.0 g.) in anhydrous dimethylformamide (200 cc.). The reaction mixture is kept at 2° C. for 2 hours and is then diluted with ice-water (3,000 cc.). The precipitate obtained is filtered off, washed three times with distilled water (total 600 cc.) and dried by means of warm air (approximately 60° C.). The product obtained (71.0 g.), which melts at 200° C., is dissolved in methylene chloride (1,500 cc.) and the solution is filtered through silica gel (71.0 g.) contained in a column of diameter 5.8 cm. Elution is carried out using methylene chloride (4,000 cc.). This eluate is discarded. Elution is then carried out using methylene chloride (2,000 cc.), a mixture of methylene chloride and methanol (99.5–0.5 by volume; 2,000 cc.) and then a mixture of methylene chloride and methanol (99–1 volume; 6,000 cc.). These eluates are combined and evaporated to dryness under reduced pressure (20 mm.Hg). The residue (51.0 g.) is purified by recrystallisation from acetonitrile (850 cc.). 5-(4-t.-Butoxycarbonylpiperazin-1-yl)carbonyloxy-6-(7-chloro-1,8-naphthyridin-2-yl)-7-oxo-2,3,6,7-tetrahydro-5H-1,4-dithiino[2,3-c]pyrrole (38.0 g.), which melts at 242° C., a compound of general formula I, is obtained.

6-(7-Chloro-1,8-naphthyridin-2-yl)-5-hydroxy-7-oxo-2,3,6,7-tetrahydro-5H-1,4-dithiino[2,3-c]pyrrole can be prepared in the following manner:
Preparation of 2-amino-7-hydroxy-1,8-naphthyridine (m.p. above 360° C.) in accordance with S. Carboni et al, Ann. di. Chim. (Roma), 51, 883 (1964).
Preparation of 5,7-dioxo-6-(7-hydroxy-1,8-naphthyridin-2-yl)-2,3,6,7-tetrahydro-5H-1,4-dithiino[2,3-c]pyrrole (m.p. 342° C.) (13.0 g.) by the action of 2-amino-7-hydroxy-1,8-naphthyridine (8.0 g.) on 5,6-dihydro-1,4-dithiin-2,3-dicarboxylic acid anhydride (18.8 g.) in a mixture of diphenyl and diphenyl ether (26.5–73.5 by weight; 150 cc.) at 230° C. for 2 hours, in the presence of anhydrous acetic acid (0.4 cc.).
Preparation of 6-(7-chloro-1,8-naphthyridin-2-yl)-5,7-dioxo-2,3,6,7-tetrahydro-5H-1,4-dithiino[2,3-c]pyrrole (m.p. 250° C.) (9.7 g.) by the action of phosphorus oxychloride (45 cc.) on 5,7-dioxo-6-(7-hydroxy-1,8-naphthyridin-2-yl)-2,3,6,7-tetrahydro-5H-1,4-dithiino-[2,3-c]pyrrole (10.6 g.), at about 100° C., for 1 hour 45 minutes, in the presence of anhydrous dimethylformamide (1.9 cc.).
Preparation of 6-(7-chloro-1,8-naphthyridin-2-yl)-5-hydroxy-7-oxo-2,3,6,7-tetrahydro-5H-1,4-dithiino[2,3-c]pyrrole (m.p. 135° C.) (1.4 g.) by the action of potassium borohydride (0.4 g.) on 6-(7-chloro-1,8-naphthyridin-2-yl)-5,7-dioxo-2,3,6,7-tetrahydro-5H-1,4-dithiino[2,3-c]pyrrole (1.7 g.) in anhydrous methanol (16 cc.) at a temperature of about 25°–30° C.

4-Chlorocarbonyl-1-t.-butoxycarbonylpiperazine can be prepared by the simultaneous additions of solutions of 1-t.-butoxycarbonylpiperazine (40.8 g.) in anhydrous toluene (200 cc.) and of phosgene (11.2 g.) in anhydrous toluene (150 cc.) to anhydrous toluene (100 cc.), the temperature being kept at about −5° C. during this operation. After stirring for 1 hour at 2° C., the 1-t.-butoxycarbonylpiperazine hydrochloride formed during the reaction is filtered off and washed twice with anhydrous toluene (total 200 cc.). The filtrate is evaporated to dryness under reduced pressure (20 mm.Hg.). 4-Chlorocarbonyl-1-t.-butoxycarbonylpiperazine (24.8 g.), which melts at 98° C., is obtained. After the product has been purified by recrystallisation from diisopropyl ether, it melts at 99° C.

1-t.-Butoxycarbonylpiperazine can be prepared by heating a mixture of a solution of anhydrous piperazine (310.0 g.) in hydrochloric acid (d=1.19) (306 cc.) and distilled water (1,000 cc.) and of a solution of t.-butyl azidoformate (259.0 g.) in dioxan (2,000 cc.) for 8 hours at 45° C. 1,4-Bis-t.-butoxycarbonylpiperazine (173.0 g.), which melts at 166° C., is isolated by filtration of the reaction mixture and then further filtration after having reduced the initial filtrate to a quarter of its volume by concentration under reduced pressure (20 mm.Hg). The filtrate is washed with chloroform (120 cc.) and then rendered alkaline by addition of 10N aqueous sodium hydroxide solution. The oil which separates out is extracted with methylene chloride (500 cc.), and the aqueous phase is saturated with sodium chloride and extracted again twice with diethyl ether (total 600 cc.). The combined organic extracts are dried over anhydrous sodium sulphate and evaporated under reduced pressure (50 mm.Hg). 1-t.-Butoxycarbonylpiperazine (46.2 g.), which melts at 41° C., is obtained.

EXAMPLE 37

Following the procedure of Example 36 but starting with 6-(7-chloro-1,8-naphthyridin-2-yl)-7-oxo-5-(piperazine-1-yl)carbonyloxy-2,3,6,7-tetrahydro-5H-1,4-dithiino[2,3-c]pyrrole (2.50 g.), N,N'-dicyclohexylcarbodiimide (1.67 g.) and methacrylic acid (0.70 g.) in anhydrous methylene chloride (50 cc.), 6-(7-chloro-1,8-naphthyridin-2-yl)-5-(4-methacryloylpiperazin-1-yl)-carbonyloxy-7-oxo-2,3,6,7-tetrahydro-5H-1,4-dithiino-[2,3-c]pyrrole (1.87 g.), which melts at 240° C., is obtained.

EXAMPLE 38

Following the procedure of Example 31 but starting with 6-(7-chloro-1,8-naphthyridin-2-yl)-7-oxo-5-(piperazin-1-yl)carbonyloxy-2,3,6,7-tetrahydro-5-H-1,4-dithiino[2,3-c]pyrrole (6.0 g.), N,N'-dicyclohexylcarbodiimide (4.0 g.) and acrylic acid (1.4 g.) in anhydrous methylene chloride (120 cc.), 5-(4-acryloylpiperazin-1-yl)carbonyloxy-6-(7-chloro-1,8-naphthyridin-2-yl)-7-oxo-2,3,6,7-tetrahydro-5H-1,4-dithiino[2,3-c]-pyrrole (1.52 g.), which melts at 250° C., is obtained.

EXAMPLE 39

6-(7-Chloro-1,8-naphthyridin-2-yl)-5-hydroxy-7-oxo-2,3,6,7-tetrahydro-5H-1,4-dithiino[2,3-c]pyrrole (2.5 g.) is added, at 0° C., to a suspension of sodium hydride (0.20 g.) in anhydrous dimethylformamide (10 cc.). The reaction mixture is stirred for 1 hour at 2° C., and then a solution of 1-acetyl-4-chlorocarbonylpiperazine (2.85 g.) in anhydrous dimethylformamide (20 cc.) is added. After 18 hours at 2° C., the reaction mixture is diluted with distilled water (100 cc.). The precipitate formed is filtered off, washed with distilled water (10 cc.) and dried in air. The product obtained (3.5 g.) is dissolved in chloroform (50 cc.), and the solution is filtered through silica gel (50.0 g.) contained in a column of diameter 4.1 cm. Elution is carried out using a mixture of chloroform and methanol (98–2 by volume; 400 cc.), and the eluate is discarded. Elution is continued using a similar mixture (400 cc). This eluate is evaporated to dryness under reduced pressure (20 mm.Hg). The chromatographed product is purified by recrystallisation from a mixture of dimethylformamide and ethanol (50–50 by volume; 20 cc.). 5-(4-Acetylpiperazin-1-yl)carbonyloxy-6-(7-chloro-1,8-naphthyridin-2-yl)-7-oxo-2,3,6,7-tetrahydro-5H-1,4-dithiino[2,3-c]pyrrole (1.40 g.), which melts at 271° C., is obtained.

1-Acetyl-4-chlorocarbonylpiperazine can be prepared by the action of phosgene (9.9 g.) on 1-acetylpiperazine (25.6 g.) in anhydrous toluene (75 cc.) for 1 hour at 2° C. The 1-acetylpiperazine hydrochloride formed during the reaction is filtered off and washed with anhydrous toluene (50 cc.). The toluene filtrate is evaporated to dryness under reduced pressure (20 mm.Hg) to give 1-acetyl-4-chlorocarbonylpiperazine (14.0 g.) in the form of an oil.

EXAMPLE 40

Propionic acid (2.68 cm$^3$) is added to a suspension of 6-(7-chloro-1,8-naphthyridin-2-yl)-7-oxo-5(1-piperazinyl) carbonyloxy-2,3,6,7-tetrahydro-5H-1,4-dithiino[2,3-c]pyrrole (11 g.) and dicyclohexylcarbodiimide (7.35 g.) in anhydrous methylene chloride (220 cm$^3$) and the mixture is stirred for one hour at 25° C. The dicyclohexyl urea formed is removed by filtration and the filtrate is washed with methylene chloride (30 cm$^3$) and evaporated to remove the solvent. The product obtained (18.0 g.) is washed with boiling ethanol (150 cm$^3$) and then recrystallised from acetonitrile (400 cm$^3$). 6-(7-Chloro-1,8-naphthyridin-2-yl)-7-oxo-5-(4-propionyl-1-piperazinyl)-carbonyloxy-2,3,6,7-tetrahydro-5H-1,4-dithiino[2,3-c]pyrrole (7.9 g.), m.p. 222° C. is thus obtained.

EXAMPLE 41

Triethylamine (2.8 cm$^3$) is added at 10° C., to a suspension of 6-(7-chloro-1,8-naphthyridin-2-yl)-5-hydroxy-7-oxo-2,3,6,7-tetrahydro-5H-1,4-dithiino[2,3-c]pyrrole (7.0 g.) and 1-chlorocarbonyl-4-propionylpiperazine (8.9 g.) in a mixture of anhydrous methylene chloride (70 cm$^3$) and anhydrous pyridine (35 cm$^3$). The reaction mixture is agitated at 20° C. for 2 hours and then diluted by addition of methylene chloride (150 cm$^3$). The organic phase is washed 5 times with a total of 300 cm$^3$ of distilled water, dried over anhydrous magnesium sulphate and evaporated. The product obtained (11.0 g.) is washed with ethanol (25 cm$^3$) and then dissolved in dimethylformamide (300 cm$^3$) at 100° C. Ethanol (15 cm$^3$) is added. After 1 hour's cooling at 2° C., the crystals which have appeared are separated by filtration, washed twice with a total of 10 cm$^3$ of ice-cold ethanol, and dried under reduced pressure (0.2 mm.Hg). 6-(7-Chloro- 1,8-naphthyridin-2-yl)-7-oxo-5-(4-propionyl-1-piperazinyl)-carbonyloxy-2,3,6,7-tetrahydro-5H-1,4-dithiino[2,3-c]pyrrole (7.9 g.), m.p. 222° C., is thus obtained.

The 1-chlorocarbonyl-4-propionylpiperazine used as starting material can be prepared as follows. Anhydrous piperazine (120 g.) and propionamide (m.p. 80° C., 102 g.) in anhydrous xylene (100 cm$^3$) are heated under reflux for 48 hours in the presence of iodine (0.9 g.) to give 1-propionylpiperazine hydrochloride (153.0 g.), m.p. 165° C. 1-Propionylpiperazine is liberated from its hydrochloride by the action of an excess of ammonia in diethyl ether. The ammonium chloride formed is separated by filtration and the 1-propionylpiperazine is isolated by evaporation of the ether.

A solution of phosgene (45.0 g.) in anhydrous toluene (500 cm$^3$) and 1-propionylpiperazine (129.0 g.) are added simultaneously to anhydrous toluene (500 cm$^3$), while the temperature is maintained at about −5° C. 1-Chlorocarbonyl-4-propionylpiperazine (92.0 g.), m.p. about 45° C., is thus obtained. After one hour's stirring at 2° C., the 1-propionylpiperazine hydrochloride formed is separated by filtration and, after evaporation of the filtrate under reduced pressure (20 mm.Hg) 1-chlorocarbonyl-4-propionyl-piperazine is obtained.

The present invention includes within its scope pharmaceutical compositions comprising, as active ingredient, at least one of the compounds of general formula I in association with a pharmaceutical carrier or coating. The invention includes especially such preparations made up for oral, parenteral, rectal or percutaneous administration.

Solid compositions for oral administration include tablets, pills, powders and granules. In such solid compositions the active compound is admixed with at least one inert diluent such as sucrose, lactose or starch. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water or liquid paraffin. Besides inert diluents such compositions may also comprise adjuvants, such as wetting, emulsifying and suspending agents, and sweetening, flavouring and aromatizing agents. The compositions according to the invention, for oral administration, also include capsules of absorbable material such as gelatin containing the active substance with or without the addition of diluents or excipients.

Preparations according to the invention for parenteral administration include sterile aqueous or non-aqueous solutions, suspensions or emulsions. Examples of non-aqueous solvents or vehicles are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilized by, for example, filtration through a bacteria-retaining filter, by incorporation in the compositions of sterilizing agents, by irradiation, or by heating. They may also be manufactured in the form of sterile solid compositions, which can be dissolved in sterile water or some other sterile injectable medium immediately before use.

Compositions for rectal administration are suppositories which contain, in addition to the active substance, excipients such as cacao butter or a suitable wax base.

The percentage of active ingredient in the compositions of the invention may be varied, it being necessary that it should constitute a proportion such that a suitable dosage shall be obtained. The dosage depends on the desired therapeutic effect, on the route of administration and on the duration of the treatment. In human therapy the compositions when administered orally to an adult should generally give doses between 10 mg. and 500 mg. of active substance per day. In general the physician will decide the posology considered appropriate, taking into account the age and weight and other factors intrinsic to the patient being treated.

The following Examples illustrate pharmaceutical compositions according to the invention.

EXAMPLE 42

Tablets containing 25 mg. of active product and having the following composition are prepared in accordance with the usual technique:

| | |
|---|---|
| 2-(7-chloro-1,8-naphthyridin-2-yl)-3-(4-acryloylpiperazin-1-yl)carbonyloxy-isoindolin-1-one | 0.025 g. |
| starch | 0.090 g. |
| precipitated silica | 0.030 g. |
| magnesium stearate | 0.005 g. |

EXAMPLE 43

Tablets containing 25 mg. of active product and having the following composition are prepared in accordance with the usual technique:

| | |
|---|---|
| 2-(7-chloro-1,8-naphthyridin-2-yl)-3-(4-methacryloylpiperazine-1-yl)carbonyloxy-isoindolin-1-one | 0.025 g. |
| starch | 0.090 g. |
| precipitated silica | 0.030 g. |
| magnesium stearate | 0.005 g. |

EXAMPLE 44

Tablets containing 25 mg. of active product and having the following composition are prepared in accordance with the usual technique:

| | |
|---|---|
| 2-(7-chloro-1,8-naphthyridin-2-yl)-3-(4-propionylpiperazin-1-yl)carbonyloxy-isoindolin-1-one | 0.025 g. |
| starch | 0.090 g. |
| precipitated silica | 0.030 g. |
| magnesium stearate | 0.005 g. |

EXAMPLE 45

Tablets containing 25 mg. of active product and having the following composition are prepared in accordance with the usual technique:

| | |
|---|---|
| 2-(7-chloro-1,8-naphthyridin-2-yl)-3-(4-trifluoroacetylpiperazin-1-yl)carbonyloxy-isoindolin-1-one | 25 mg. |
| starch | 90 mg. |
| precipitated silica | 30 mg. |
| magnesium stearate | 5 mg. |

EXAMPLE 46

Tablets containing 25 mg. of active product and having the following composition are prepared in accordance with the usual technique:

| | |
|---|---|
| 3-(4-butyrylpiperazin-1-yl)carbonyloxy-2-(7-chloro-1,8-naphthyridin-2-yl)-isoindolin-1-one | 25 mg. |
| starch | 90 mg. |
| precipitated silica | 30 mg. |
| magnesium stearate | 5 mg. |

Instead of the isoindolinone derivatives mentioned in Examples 42 to 46 there may be incorporated in similarly formulated tablets other heterocyclic compounds conforming to general formula I, for example 5-(4-acetylpiperazin-1-yl)carbonyloxy-6-(7-chloro-1,8-naphthyridin-2-yl)-7-oxo-6,7-dihydro-5H-pyrrolo[3,4-b]-pyrazine, 5-(4-acryloylpiperazin-1-yl)carbonyloxy-6-(5-chloropyrid-2-yl)-7-oxo-6,7-dihydro-5H-pyrrolo[3,4-b]-pyrazine, 5-(4-acryloylpiperazin-1-yl)carbonyloxy-6-(7-chloro-1,8-naphthyridin-2-yl)-7-oxo-2,3,6,7-tetrahydro-5H-1,4-oxathiino[2,3-c]pyrrole, 5-(4-acryloylpiperazin-1-yl)carbonyloxy-6-(7-chloro-1,8-naphthyridin-2-yl)-7-oxo-2,3,6,7-tetrahydro-5H-1,4-dithiino[2,3-c]pyrrole, and 6-(7-chloro-1,8-naphthyridin-2-yl)-7-oxo-5-(4-propionylpiperazin-1-yl)carbonyloxy-2,3,6,7-tetrahydro-5H-1,4-dithiino[2,3-c]pyrrole.

We claim:

1. A heterocyclic compound of the formula:

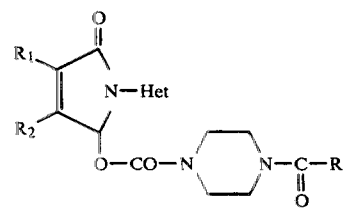

wherein the pyrroline ring and the symbols $R_1$ and $R_2$ together form an isoindoline, 2,3,6,7-tetrahydro-5H-1,4-oxathiino-[2,3-c]-pyrrole, or 2,3,6,7-tetrahydro-5H-1,4-dithiino-[2,3-c]-pyrrole nucleus, Het represents 1,8-naphthyridin-2-yl substituted by a chlorine atom, and R represents hydrogen, alkyl of 1 through 4 carbon atoms, alkenyl of 2 through 4 carbon atoms or trifluoromethyl.

2. A pharmaceutical composition useful as a tranquilliser, anti-convulsant agent, decontracturant or hypnotic agent which comprises, as active ingredient, an effective amount of a heterocyclic compound of the formula depicted in claim 1 wherein $R_1$, $R_2$, Het, and R have the meanings specified in claim 1 in association with a pharmaceutical carrier.

3. A heterocyclic compound of the formula:

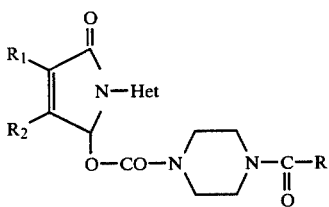

wherein the pyrroline ring and the symbols $R_1$ and $R_2$ together form an isoindoline or 2,3,6,7-tetrahydro-5H-1,4-dithiino[2,3-c]-pyrrole nucleus, Het represents 1,8-naphthyridin-2-yl substituted by a chlorine atom, and R represents hydrogen, alkyl of 1 through 4 carbon atoms, alkenyl of 2 through 4 carbon atoms, or trifluoromethyl.

4. A heterocyclic compound according to claim 3 wherein Het represents 7-chloro-1,8-naphthyridin-2-yl.

5. A pharmaceutical composition useful as a tranquilizer, anti-convulsant agent, decontracturant, or hypnotic agent, which comprises as active ingredient an effective amount of a heterocyclic compound of the formula depicted in claim 3, wherein $R_1$, $R_2$, Het, and R have the meanings specified in claim 3, in association with a pharmaceutical carrier.

6. The heterocyclic compound according to claim 3 which is 3-(4-acryloylpiperazin-1-yl)carbonyloxy-2-(7-chloro-1,8-naphthyridin-2-yl)-isoindolin-1-one.

7. The heterocyclic compound according to claim 3 which is 2-(7-chloro-1,8-naphthyridin-2-yl)-3-(4-methacryloylpiperazin-1-yl)carbonyloxy-isoindolin-1-one.

8. The heterocyclic compound according to claim 3 which is 2-(7-chloro-1,8-naphthyridin-2-yl)-3-(4-propionylpiperazin-1-yl)carbonyloxy-isoindolin-1-one.

9. The heterocyclic compound according to claim 3 which is 2-(7-chloro-1,8-naphthyridin-2-yl)-3-(4-trifluoroacetylpiperazin-1-yl)carbonyloxy-isoindolin-1-one.

10. The heterocylic compound according to claim 3 which is 3-(4-butyrylpiperazin-1-yl)carbonyloxy-2-(7-chloro-1,8-naphthyridin-2-yl)-isoindolin-1-one.

11. The heterocyclic compound according to claim 3 which is 2-(7-chloro-1,8-naphthyridin-2-yl)-3-(4-formylpiperazin-1-yl)carbonyloxy-isoindolin-1-one.

12. The heterocyclic compound according to claim 3 which is 2-(7-chloro-1,8-naphthyridin-2-yl)-3-[4-(3-methyl-but-2-enoyl)-piperazin-1-yl]carbonyloxyisoindolin-1-one.

13. The heterocylic compound according to claim 3 which is 2-(7-chloro-1,8-naphthyridin-2-yl)-7-oxo-5-(4-propionyl-piperazin-1-yl)-carbonyloxy-2,3,6,7-tetrahydro-5H-1,4-dithiino[2,3-c]pyrrole.

* * * * *